US012742787B2

(12) United States Patent
Muntendam et al.

(10) Patent No.: US 12,742,787 B2
(45) Date of Patent: Sep. 22, 2026

(54) GALECTIN-3 IMMUNOASSAY

(71) Applicant: BG Medicine, Inc., Waltham, MA (US)

(72) Inventors: Pieter Muntendam, Boxford, MA (US); Shunguang Wang, Carlisle, MA (US)

(73) Assignee: BG Medicine, Inc., Waltham, MA (US)

( * ) Notice: Subject to any disclaimer, the term of this patent is extended or adjusted under 35 U.S.C. 154(b) by 619 days.

(21) Appl. No.: 18/126,055

(22) Filed: Mar. 24, 2023

(65) Prior Publication Data

US 2024/0103018 A1 Mar. 28, 2024

Related U.S. Application Data

(63) Continuation of application No. 16/444,402, filed on Jun. 18, 2019, now abandoned, which is a continuation of application No. 15/424,306, filed on Feb. 3, 2017, now abandoned, which is a continuation of application No. 12/608,821, filed on Oct. 29, 2009, now abandoned.

(60) Provisional application No. 61/109,366, filed on Oct. 29, 2008.

(51) Int. Cl.

| | |
|---|---|
| ***G01N 33/577*** | (2006.01) |
| ***G01N 33/68*** | (2006.01) |
| ***G01N 33/92*** | (2006.01) |

(52) U.S. Cl.

CPC ....... *G01N 33/6893* (2013.01); *G01N 33/577* (2013.01); *G01N 33/92* (2013.01); *G01N 2333/4724* (2013.01); *G01N 2800/325* (2013.01)

(58) Field of Classification Search

CPC ............. G01N 33/577; G01N 33/6893; G01N 2333/4724; G01N 2800/325; G01N 33/53; G01N 33/92; C07K 16/2851; C07K 16/18

See application file for complete search history.

(56) References Cited

U.S. PATENT DOCUMENTS

| | | | | |
|---|---|---|---|---|
| 4,632,901 | A | 12/1986 | Valkirs et al. | |
| 4,704,692 | A | 11/1987 | Ladner | |
| 4,946,778 | A | 8/1990 | Ladner et al. | |
| 5,091,513 | A | 2/1992 | Huston et al. | |
| 5,132,405 | A | 7/1992 | Huston et al. | |
| 6,319,676 | B1 | 11/2001 | Nazareth et al. | |
| 6,485,982 | B1 | 11/2002 | Charlton | |
| 6,534,322 | B1 | 3/2003 | Sabbadini | |
| 6,889,083 | B2 | 5/2005 | Kleckner et al. | |
| 7,041,449 | B2 * | 5/2006 | Prolla | C12Q 1/6809 435/7.1 |
| 7,888,137 | B2 * | 2/2011 | Pinto | G01N 33/6893 436/811 |
| 8,084,276 | B2 | 12/2011 | Pinto | |
| 8,672,857 | B2 | 3/2014 | Muntendam | |
| 2002/0044932 | A1 * | 4/2002 | Liu | A61P 29/00 424/143.1 |
| 2002/0076738 | A1 | 6/2002 | Woo | |
| 2002/0155513 | A1 | 10/2002 | Hsu et al. | |
| 2003/0032030 | A1 | 2/2003 | Prolla et al. | |
| 2003/0166017 | A1 | 9/2003 | McCarthy | |
| 2004/0110221 | A1 | 6/2004 | Twine et al. | |
| 2005/0084915 | A1 | 4/2005 | Woo | |
| 2005/0106100 | A1 | 5/2005 | Harris et al. | |
| 2006/0019235 | A1 | 1/2006 | Soen et al. | |
| 2006/0019890 | A1 | 1/2006 | Kapoun et al. | |
| 2006/0141493 | A1 | 6/2006 | West et al. | |
| 2006/0166276 | A1 | 7/2006 | Doyle et al. | |
| 2006/0246496 | A1 | 11/2006 | Ahmed et al. | |
| 2006/0257946 | A1 | 11/2006 | Ding et al. | |
| 2007/0082332 | A1 | 4/2007 | Mendrick et al. | |
| 2007/0092886 | A1 | 4/2007 | Tabibiazar et al. | |
| 2007/0105105 | A1 | 5/2007 | Clelland et al. | |
| 2007/0274959 | A1 | 11/2007 | Zeiher et al. | |
| 2008/0193954 | A1 | 8/2008 | Pinto | |
| 2008/0208167 | A1 | 8/2008 | Stankus et al. | |
| 2010/0129927 | A1 | 5/2010 | Cleutjens et al. | |
| 2010/0143954 | A1 | 6/2010 | Muntendam | |
| 2011/0008805 | A1 | 1/2011 | Urdea et al. | |
| 2011/0071583 | A1 | 3/2011 | Muntendam | |

(Continued)

FOREIGN PATENT DOCUMENTS

| | | |
|---|---|---|
| CN | 1620612 A | 5/2005 |
| EP | 1522857 A1 | 4/2005 |

(Continued)

OTHER PUBLICATIONS

Inohara et al. Cytoplasmic and serum galectin-3 in diagnosis of thyroid malignancies. Biochem. Biophys. Res. Comm. 376: 605-610 (Sep. 2008).*

(Continued)

*Primary Examiner* — Gailene Gabel

(74) *Attorney, Agent, or Firm* — Goodwin Procter LLP

(57) ABSTRACT

The present invention relates to methods and compositions for specifically and quantitatively detecting galectin-3 in a sample. Embodiments of the invention include a detection assay in which a capture binding moiety and a labeled binding moiety specifically recognize non-overlapping epitopes on the N-terminus of galectin-3. Further embodiments are directed to a method for establishing ranges of galectin-3 concentrations indicative of the presence and severity of heart failure in a subject and a method for predicting the clinical outcome of a subject based upon galectin-3 concentration.

6 Claims, 6 Drawing Sheets

Specification includes a Sequence Listing.

(56) References Cited

U.S. PATENT DOCUMENTS

| | | | |
|---|---|---|---|
| 2011/0104722 | A1 | 5/2011 | Pinto |
| 2011/0137131 | A1 | 6/2011 | Adourian et al. |
| 2012/0029003 | A1 | 2/2012 | Muntendam |
| 2012/0220532 | A1 | 8/2012 | Pinto |
| 2012/0220671 | A1 | 8/2012 | Muntendam |
| 2013/0029955 | A1 | 1/2013 | Muntendam |
| 2013/0189716 | A1 | 7/2013 | Pinto |
| 2013/0344517 | A1 | 12/2013 | Muntendam |
| 2015/0037353 | A1 | 2/2015 | Pinto |
| 2017/0370944 | A1 | 12/2017 | Muntendam et al. |

FOREIGN PATENT DOCUMENTS

| | | | |
|---|---|---|---|
| JP | 2004198313 | A | 7/2004 |
| WO | WO-0177389 | A2 | 10/2001 |
| WO | WO-03031650 | A2 | 4/2003 |
| WO | WO-03071279 | A1 | 8/2003 |
| WO | WO-2004038376 | A2 | 5/2004 |
| WO | WO-2004048933 | A2 | 6/2004 |
| WO | WO-2004063334 | A2 | 7/2004 |
| WO | WO-2004111654 | A2 | 12/2004 |
| WO | WO-2005023314 | A1 | 3/2005 |
| WO | WO-2005040817 | A1 | 5/2005 |
| WO | WO-2005070446 | A1 | 8/2005 |
| WO | WO-2006026074 | A2 | 3/2006 |
| WO | WO-2006083986 | A2 | 8/2006 |
| WO | WO-2010096126 | A1 | 8/2010 |
| WO | WO-2011031493 | A2 | 3/2011 |
| WO | WO-2012003475 | A1 | 1/2012 |
| WO | WO-2012106341 | A1 | 8/2012 |
| WO | WO-2012162531 | A1 | 11/2012 |
| WO | WO-2013103984 | A2 | 7/2013 |

OTHER PUBLICATIONS

Lurisci et al. Concentrations of Galectin-3 in the Sera of Normal Controls and Cancer Patients. Clin. Cancer Res. 6: 1389 (2000).*

Aragno et al. (2006) "Oxidative Stress-Dependent Impairment of Cardiac-Specific Transcription Factors in Experimental Diabetes," Endocrinology 147(12):5967-5974.

Bender MedSystems product information and manual for enzyme-linked immunosorbent assay for quantitative detection of human Galectin-3, BMS279/2, dated Aug. 24, 2006, 32 pages.

Bohlender et al. (2005) "Advanced glycation end products and the kidney," American Journal of Physiology: Renal Physiology 289: F645-F659.

Cameselle-Teijeiro et al. (2005) "Cystic tumor of the atrioventricular node of the heart appears to be the heart equivalent of the solid cell nests (ultimobranchial rests) of the thyroid," American Journal of Clinical Pathology 123(3): 369-375.

Cheng et al. (2007) "Differential neuroprotective effects of a minocycline-based drug cocktail in transient and permanent focal cerebral ischemia," Experimental Neurology 204(1): 433-442.

Lurisci et al. (2000) "Concentrations of Galectin-3 in the Sera of Normal Controls and Cancer Patients," Clinical Cancer Research 6:1389-1393.

Kankova et al. (2005) "Haplotype Analysis of the RAGE gene: Identification of a Haplotype Marker for Diabetic Nephropathy in Type 2 Diabetes Mellitus," Nephrology, Dialysis, Transplantation 20(6): 1093-1102.

Karlsen et al. (2006) "Immune-mediated beta-cell destruction in vitro and in vivo—A pivotal role for galectin-3," Biochemical and Biophysical Research Communications 344(1): 406-415.

Liehn et al. (2005) "CCR5-but not CCR1-deficiency protects against neointima formation in apolipoprotein E-deficient mice," European Heart Journal 26(Suppl 1): 239.

Lok et al. (2007) "Galectin-3, a novel marker of macrophage activity, predicts outcome in patients with stable chronic heart failure," Journal of the American College of Cardiology 49(9) Suppl. A: 98A.

Mensah-Brown et al. (2006) "Functional Capacity of Macrophages Determines the Induction of Type 1 Diabetes," Annals of the New York Academy of Sciences 1084: 49-57.

Mita et al. (2007) "Swings in blood glucose levels accelerate atherogenesis in apolipoprotein E-deficient mice," Biochemical and Biophysical Research Communications 358(3): 679-685.

Moore et al. (2005) "Using Peripheral Blood Mononuclear Cells to Determine a Gene Expression Profile of Acute Ischemic Stroke: A Pilot Investigation," Circulation 111(2):212-221.

Papaspyridonos et al. (2006) "A Potential Role for Galectin-3 in Atherosclerotic Plaque Progression through Monocyte Chemoattraction and Macrophage Activation" Atherosclerosis 186(2):S3.

Pieters (2006) "Inhibition and Detection of Galectins," ChemBioChem 7:721-728.

Pugliese et al. (2006) "Increased Glomerular Cell (Podocyte) Apoptosis in Rats with Streptozotocin-induced Diabetes Mellitus: Relation to Increased p53 Expression," Diabetologia 49(Suppl 1):651-652.

Reifenberg et al. (2007) "Interferon-gamma Induces Chronic Active Myocarditis and Cardiomyopathy in Transgenic Mice," American Journal of Pathology 171(2): 463-472.

Schroen et al. (2003) "Genomic analysis identifies Thrombospondin-2 as a molecular predictor of heart failure," Circulation 108(17 Suppl.):IV-260.

Schroen et al. (2007) "Lysosomal Integral Membrane Protein 2 is a Novel Component of the Cardiac Intercalated Disc and Vital for Load-induced Cardiac Myocyte Hypertrophy," Journal of Experimental Medicine 204(5): 1227-1235.

Sharma et al. (2003) "Galectin-3 is a novel macrophage derived mediator of cardiac fibrosis and specifically marks failing hearts," Circulation 108(17 Suppl.):IV-261.

Sharma et al. (2004) "Galectin-3 Marks Activated Macrophages in Failure-Prone Hypertrophied Hearts and Contributes to Cardiac Dysfunction," Circulation 110:3121-3128.

Sharma et al. (2005) "Early growth regulator-1 mediates galectin-3 induced cardiac fibrosis," Hypertension 46:819-820.

Sharma et al. (2005) "Mice lacking galectin-3 exhibit preserved cardiac function and decreased fibrosis following angiotensin II infusion," Circulation 112(17) Suppl S:II-64.

Sharma et al. (2007) "Novel Anti-inflammatory Mechanisms of Ac-SDKP in High Blood Pressure-induced Target Organ Damage," Circulation 114(18) Suppl S:240.

Shirakata et al. (2001) Inverse regulation of the angiogenesis factor VEGF and the angiogenesis inhibitors Thrombospondin-1 and TSP-2 in human epidermal keratinocytes, Journal of Investigative Dermatology 117(2):391.

Stitt et al. (2005) "Impaired Retinal Angiogenesis in Diabetes: Role of Advanced Glycation End Products and Galectin-3," Diabetes 54(3):785-794.

Tan et al. (2007) "AGE, RAGE and ROS in Diabetic Neuropathy," Seminars in Nephrology 27(2):130-143.

Tang et al. (2007) "National Academy of Clinical Biochemistry Laboratory Medicine Practice Guidelines; Clinical Utilization of Cardiac Biomarker Testing in Heart Failure," Circulation 116(5):e99-e109.

Van Kimmenade et al. (2005) "Galectin-3 predicts 60 days mortality in heart failure: A step towards multimarker strategy in heart failure. Results from the ProBNP investigation of dyspnea in the emergency department (PRIDE) study," Circulation 112(17) Suppl S:II-669.

Van Kimmenade et al. (2006) "Utility of amino-terminal pro-brain natriuretic peptide, galectin-3, and apelin for the evaluation of patients with acute heart failure," Journal of the American College of Cardiology 48(6):1217-1224.

Walton et al. (2003) "Thrombospondin-2 and lymphotoxin-alpha gene variations predict coronary heart disease in a large prospective study," Circulation 108(17 Suppl.):IV-260.

Barboni et al. (2005) "The binding of mycolic acids to galectin-3: A novel interaction between a host soluble lectin and trafficking mycobacterial lipids?" FEBS Letters 579:6749-6755.

Bender MedSystems product information and manual for enzyme-linked immunosorbent assay for quantitative detection of human Galectin-3, BMS279/2CE and BMS-279/2TENCE, dated Mar. 26, 2008, 36 pages.

(56) References Cited

OTHER PUBLICATIONS

Cherayil et al. (1990) "Molecular cloning of a human macrophage lectin specific for galactose," Proc. Natl. Acad. Sci. USA 87:7324-7328.
Hrdlickova-Cela et al. (2001) "Detection of galectin-3 in tear fluid at disease states and immunohistochemical and lectin histochemical analysis in human corneal and conjunctival epithelium," Br J Ophthalmol 85:1336-1340.
Ingrassia et al. (2006) "Anti-Galectin Compounds as Potential Anti-Cancer Drugs," Current Medicinal Chemistry 13:3513-3527.
Jensen-Jarolim et al. (2001) "Anti-Galectin-3 IgG autoantibodies in patients with Crohn's disease characterized by means of phage display peptide libraries," J Clin Immunol 21:348-356.
Lim et al. (2002) "Identification of autoantibodies associated with systemic lupus erythmatosus," Biochem Biophys Res Commun 295:119-124.
Liu et al. (1996) "Modulation of functional properties of galectin-3 by monoclonal antibodies binding to the non-lectin domains," Biochemistry 35:6073-6079.
Mathews et al. (1995) "Evidence for IgG autoantibodies to galectin-3, a beta-galactosidase-binding lectin (Mac-2, epsilon binding protein, or carbohydrate binding protein 35) in human serum," J Clin Immunol 15:329-337.
Nachtigal et al. (1998) "Galectin-3 Expression in Human Atherosclerotic Lesions," American Journal of Pathology 152(5): 1199-1208.
Schroen et al. (2004) "Thrombospondin-2 Is Essential for Myocardial Matrix Integrity," Circulation Research 95:515-522.
Wada et al. (2001) "Galectins, Galactoside-Binding Mammalian Lectins: Clinical Application of Multi-Functional Proteins," Acta. Med. Okayama 55(1):11-17.
Demetter et al. (2008) "The galectin family and digestive disease," J. Path. 215:1-12.
André et al. (2001) "Wedgelike Glycodendrimers as Inhibitors of Binding of Mammalian Galectins to Glycoproteins, Lactose Maxiclusters, and Cell Surface Glycoconjugates," ChemBioChem. ChemBioChem. 2:822-830.
Inohara et al. 2008 "Cytoplasmic and serum galectin-3 in diagnosis of thyroid malignancies," Biochek. And Biophysical Research Comm. 376:605-610.
Demetter et al. (2008) "The galectin family and digestive disease," J. Pathol. 215:1-12.
Almkvist et al. (2004) "Galectins as inflammatory mediators," Glyconconj J. 19:575-81.
André et al. (2001) "Wedgelike Glycodendrimers as Inhibitors of Binding of Mammalian Galectins to Glycoproteins, Lactos Maxiclusters, and Cell Surface Glycoconjugates," ChemBioChem. 2:822-830.
Barboni et al. (2000) "Molecular modeling and mutagenesis studies of the N-terminal domains of galectin-3: evidence for participation with the C-terminal carbohydrate recognition domain in oliogosaccharide binding," Glycobiology 10:1201-8.
Cooper, D.N. (2002) "Finding themes in complexity," Biochim Biophys Acta. 1572:209-31.
De Boer et al. (2009) "Galectin-3: a novel mediator of heart failure development and progression," Eur J Heart Fail. 11:811-17.
deFilippi et al. (2009) "Clinical validation of a novel assay for galectin-3 for risk assessment in acutely destabilized heart failure," J Card Fail. 15:S9. (Presented at the Heart Failure Society of America Annual Scientific Meeting, 2009, Boston, MA).
Dumic et al (2006) "Galectin-3: an open-ended story," Biochim Biophys Acta. 1760:616-35.
Gabius (1990) "Influence of Type of Linkage and Spacer on the Interaction of β-Galactoside-Binding Proteins with Immobilized Affinity Ligands," Analytical Biochem. 189:91-94.
Hsu et al. (1999) "Galectin-3 expression is induced in cirrhotic liver and hepatocellular carcinoma," Int J Cancer 81:519-26.
Kasper et al (1996) "Immunocytochemical evidence for a modulatin of galectin-3 (mac2), a carbohydrate binding protein, in pulmonary fibrosis," J Pathol. 179:309-16.
Kim et al. (2007) "Expression and immunohistochemical localilzatin of galectin-3 in various mouse tissues," Cell Biol Int. 31:655-62.
Lin et al. (2009) "The relationship between serum galectin-3 and serum markers of cardiac extracellular matrix turnover in heart failure patients," Clin Chim Acta. 409:96-9.
Menon et al. (1999) "Determinants in the N-terminal domains of galectin-3 for secretion by a novel pathway circumventing the endoplasmic reticulum-Golgi complex," Eur J Biochem. 264:569-76.
Milting et al. (2008) "Plasma biomarkers of myocardial fibrosis and remodeling in terminal heart failure patients supported by mechanical circulatory support devices," J Heart Lung Transplant, 27:589-96.
Muntendam et al. (2009) "Reference interval for plasma galectin-3 in healthy subjects age 55 years and older," Clin Chem. 55:B72. (Presented at the American Association for Clinical Chemistry Annual Meeting, 2009, Chicago, IL).
Ochieng et al. (2004) "Extracellular functions of galectin-3," Glycoconj J. 19:527-35.
Sano et al. (2003) "Critical role of galectin-3 in phagocytosis by macrophages," J Clin Invest. 112:389-97.
Seetharaman et al. (1998) "X-ray crystal structure of the human galectin-3 carbohydrate recognition domain at 2.1-A resolution," J Biol Chem. 273: 13047-52.
Sharma et al. (2008) "Novel anti-inflammatory mechanisms of N-acetyl-ser-asp-lys-pro in hypertension-induced target organ damage," Am J Physiol Hear Circ Physiol.294:H1226-32.
Smith et al. (2009) "Analytical performance of an optimized ELISA for galectin-3," Clin Chem. 55:B69. (Presented at the American Association for Clinical Chemistry Annual Meeting, 2009, Chicago, IL).
Van Veldhuisen et al. (2009) "Clinical and prognostic value of galectin-3, a novel fibrosis-associated biomarker, in patient with chronic heart failure," J Card Fail. 15:814.
Yang et al. (2008) "Galectins: Structure, function and therapeutic potential," Expert Rev Mol Med. 13:e17-e39.
International Search Report on Patentability and Written Opinion of the International Searching Authority for for PCT/US2009/062616 dated Jul. 6, 2010; 31 pages.
Invitation to Pay Additional Fees and, Where Applicable, Protest Fee of the International Searching Authority, dated Jul. 2, 2010; 8 pages.
Liu et al. (1995) "Expression and Function of Galectin-3, a β-Galactoside-Binding Lectin, in Human Monocytes and Macrophages," American J. Pathology. 147(4):1016-1028.
Zhu and Ochieng (2001) "Rapid Release of Intracellular Galectin-3 from Breast Carcinoma Cells by Fetuin," Cancer Research. 61:1869-1873.
Rocchiccioli et al. (2010) "Biomarkers in Heart Failure: A Clinical Review," Heart Fail Rev. 15:251-273.
Bandman et al., (2002) "Complexity of inflammatory responses in endothelial cells and vascular smooth muscle cells determined by microarray analysis," Ann. N.Y. Acad. Sci. 975:77-90.
Barondes et al., (1994) "Galectins: A family of animal b-galactoside-binding lectins," Cell. 76:597-8.
BGM Galectin-3 assay; Product Insert (US); BG Medicine, Inc., Mar. 2011.
Bolli, (2002) "Clinical strategies for controlling peaks and valleys: type 1 diabetes," IJCP. 10 pages.
Boluyt et al., (2000) "Matrix gene expression and decompensated heart failure: the aged SHR model," Cardiovascular Research. 239-249.
Boluyt et al., (1995) "The ageing spontaneously hypertensive rat as a model of the transition from stable compensated hypertrophy to heart failure," European Heart J. 16:19-30.
Boluyt et al., (1995) "The lonely failing heart: a case for ECM genes," Cardiovascular Research. 835-840.
Braunwald, (2008) "Biomarkers in heart failure," N. Engl. J. Med. 358(20):2148-59.
Broers et al., (1999) "Dynamics of the nuclear lamina as monitored by GFP-tagged A-type lamins," J. of Cell Science. 112:3463-3475.

(56) References Cited

OTHER PUBLICATIONS

Brooks et al., (1997) "Captopril modifies gene expression in hypertrophied and failing hearts of aged spontaneously hypertensive rats," Hypertension. 30:1362-1368.
Christenson et al., (2010) "Multi-center determination of galectin-3 assay performance characteristics: anatomy of a novel assay for use in heart failure," Clin. Biochem. 43:683-90.
Clackson et al., (1991) "Making antibody fragments using phage display libraries," Nature. 352:624-628.
Cleutjens et al., (1995) "Collagen remodeling after myocardial infarction in the rat heart," American J. of Pathology. 147(2):325-338.
Cleutjens et al., (1999) "Thrombospondin 2 deficiency in mice results in cardiac rupture early after myocardial infarction," Circulation. abstract.
Cohn et al., (2000) "Cardiac remodeling—concepts and clinical implications: a consensus paper from an international forum on cardiac remodeling," J. Am Coll Cardiol. 35(3):569-82.
Cosson, (2004) "Usefulness of B-type natriuretic peptide (BNP) as a screen for left ventricular abnormalities in diabetes mellitus," Diabetes Metab. 30:381-6.
Czekalski, "BNP concentrations in diabetics with dyspnea," printed on Sep. 14, 2007, 4 pages.
de Boer et al., (2010) "Clinical and prognostic value of galectin-3, a novel fibrosis-associated biomarker. Relation with clinical and biochemical correlates of heart failure," J. Am. Coll. Cardiol. 55:A26. (Presented at the American College of Cardiology Annual Scientific Session, 2010, Atlanta, GA).
de Boer et al., (2010) "Galectin-3 in cardiac remodeling and heart failure," Curr. Heart Fail. Rep. 7:1-8.
de Boer et al., (2011) "Predictive value of plasma galectin-3 levels in heart failure with reduced and preserved ejection fraction," Ann. Med. 43(1):60-68.
de Couto et al., (2010) "Early detection of myocardial dysfunction and heart failure," Nat. Rev. Cardiol. 7(6):334-44.
deFilippi et al., (2010) "Galectin-3 in heart failure-linking fibrosis, remodeling, and progression," US Cardiology. 7:67-70.
Epshteyn, (2003) "Utility of B-type natriuretic peptide (BNP) as a screen for left ventricular dysfunction in patients with diabetes," Diabetes Care. 26(7):2081-2087.
Erkilet et al., (2010) "181: Plasma galectin 3 is increased in terminal heart failure patients and is elevated in patients not surviving mechanical circulatory support," J. of Heart and Lung Transplantation. 29(2):S65.
Felker et al., (2010) "Prognostic value of galectin-3 in chronic heart failure: results from the HF-Action study." (Presented at the European Society of Cardiology Congress, 2010, Stockholm, Sweden).
Gabius, (2006) "Cell surface glycans: the why and how of their functionality as biochemical signals in lectin-mediated information transfer," Crit. Rev. Immunol. 26(1):43-79.
Giordanengo et al., (2001) "Anti-galectin-1 autoantibodies in human trypansosoma cruzi infection: differential expression of this b-galactoside-binding protein in cardiac Chagas' disease," Clinc. Exp. Immunology. 266-273.
Grandin et al., (2011) "Galectin-3 and the development of heart failure after acute coronary syndrome: A pilot experience from PROVE IT-TIMI 22," J. Am Coll Cardiol. 57(14):69.
Hagberg, (1998) "From magnetic resonance spectroscopy to classification of tumors. A review of pattern recognition methods," NMR Biomed. 11:148-156.
Hein et al., (2003) "Progression from compensated hypertrophy to failure in the pressure- overloaded human heart: structural deterioration and compensatory mechanisms," J. of the American Heart Association. 107:984-991.
Henderson et al., (2008) "Galectin-3 expression and secretion links macrophages to the promotion of renal fibrosis," Am. J. Pathol. 172(2):288-98.
Henderson et al., (2006) "Galectin-3 regulates myofibroblast activation and hepatic fibrosis," Proc. Natl. Acad. Sci. USA. 103(13):5060-5065.
Henderson and Sethi, (2009) "The regulation of inflammation by galectin-3," Immunol. Rev. 230:160-71.
International Search Report and Written Opinion for International Application No. PCT/EP2004/010879, mailed Nov. 25, 2004, 14 pages.
International Preliminary Report, for International Application No. PCT/EP2004/10879, mailed Sep. 20, 2005.
International Search Report and Written Opinion for International Application No. PCT/US2010/046689 dated May 18, 2011, 10 pages.
International Search Report and Written Opinion for International Application No. PCT/US2011/042846 dated Oct. 20, 2011, 11 pages.
Kolatsi-Joannou et al., (2011) "Modified citrus pectin reduces galectin-3 expression and disease severity in experimental acute kidney injury," PLoS One. 6(4):e18683 1-9.
Kostin et al., (2003) "Mycocytes die by multiple mechanisms in failing human hearts," Circulation Research. 1-11.
Kuwabara et al., (1996) "Galectin-3 promotes adhesion of human neutrophils to laminin," J. Immunol. 156(10):3939-3944.
Lainscak et al., (2010) "Clinical trials update from the Heart Failure Society of America Meeting 2009: Fast, IMPROVE-HF, COACH galectin-3 substudy, HF-ACTION nuclear substudy, DAD-HF, and MARVEL-1," Eur. J. Heart Fail. 12(2):193-6.
Lambert et al., (2008) "Macrophage roles following myocardial infarction," Int. J. Cardiol. 130:147-58.
Liu et al., (2009) "Angiotensin-converting enzyme is a modifier of hypertensive end organ damage," J. of Biological Chemistry. 284(23):15564-15572.
Liu et al., (2009) "N-acetyl-seryl-aspartyl-lysyl-proline prevents cardiac remodeling and dysfunction induced by galectin-3, a mammalian adhesion/growth-regulatory lectin," Am J Physiol Heart Circ Physiol. 296:H404-12.
Lok et al., (2010) "Plasma galectin-3 levels predict left ventricular remodelling determined by sequential echocardiography: results from the Deventer-Alkmaar heart failure study," J. Am Coll Cardiol. 55(10):A17. (Presented at the American College of Cardiology Annual Scientific Session, 2010, Atlanta, GA).
Lok et al., (2010) "Prognostic value of galectin-3, a novel marker of fibrosis, in patients with chronic heart failure: data from the DEAL-HF study," Clin. Res. Cardiol. 99:323-8.
Lok et al., (2007) "Relationship between galectin-3 and NT pro-BNP and outcome in patients with chronic congestive heart failure," Eur. Heart J. 28: 141, Abstract 1035, http:/cic.escardio.org/abstractdetails.aspx?id-50976&eevtid-19, 1 page.
Lorell and Carabello, (2000) "Left ventricular hypertrophy: pathogenesis, detection, and prognosis," Circulation. 102:470-479.
Luft et al., (1999) "Hypertension-induced end-organ damage: a new transgenic approach to an old problem," Hypertension. 33:212-218.
Lukyanov et al., (2005) "Galectin-3 interacts with membrane lipids and penetrates the lipid bilayer," Biochem Biophys Res Commun. 338:1031-6.
McCowan et al., "Hypertensive Emergencies," Emedicine. (2009) 1-23.
Nesto et al., (2003) "Thiazolidinedione use, fluid retention, and congestive heart failure: a consensus statement from the American Heart Association and American Diabetes Association," Circulation. 108(23):2941-2948.
Nesto, (2007) "CHF in diabetes: implications for the use of TZDs (Slides with Transcript)," http://cme.medscape.com/viewarticle560872_print, 17 pages.
Nishi et al., (2007) "Role of galectin-3 in human pulmonary fibrosis," Allergol. Int. 56:57-65.
Ogawa et al., (2003) "Plasma BNP levels in the treatment of type 2 diabetes with Pioglitazone," The J. of Clinical Endocrinology & Metabolism. 88(8):3993-3996.
Opie et al., (2006) "Controversies in ventricular remodelling," Lancet. 367:356-67.
"Panel Discussion (Slides with Transcript)," published Aug. 8, 2007, http://cme.medscape.com/viewarticle/560873, 6 pages.
Panidis et al., (1984) "Development and regression of left ventricular hypertrophy," J. by the American College of Cardiology. 3(5):1309-20.

(56) References Cited

OTHER PUBLICATIONS

Papaspyridonos et al. (2008) "Galectin-3 Is an Amplifier of Inflammation in Atherosclerotic Plaque Progression Through Macrophage Activation and Monocyte Chemoattraction," Arterioscler. Thromb. Vasc. Biol. 28(3):433-440.

Plutzky, (2007) "What do we know about surrogate markers and disease outcomes? (Slides with transcript)," http://cme.medscape.com/viewarticle/560871_print, 13 pages.

Pokharel et al., (2002) "N-Acetyl-Ser-Asp-Lys-Pro inhibits phosphorylation of smad2 in cardiac fibroblasts," Hypertension. 155-161.

Psarras et al., (2011) "Regulation of adverse remodelling by osteopontin in a genetic heart failure model," Eur Heart J. epub Jul. 20, 2011, 1-10.

Rossignol et al., (2010) "Galectin-3 and PIIINP are associated with cardiovascular outcomes in patients with heart failure, left ventricular dysfunction and dysynchrony. Insights from the Care- Hf study," P2479 (Presented at the European Society of Cardiology Congress, 2010, Stockholm, Sweden).

Sano et al., (2000) "Human galectin-3 is a novel chemoattractant for monocytes and macrophages," J. Immunol. 165(4):2156-2164.

Sasaki et al., (1999) "Galectin-3 modulates rat mesangial cell proliferation and matrix synthesis during experimental glomerulonephritis induced by anti-Thy1.1 antibodies," J. Pathol. 187:481-9.

Sathisha et al., (2007) "Inhibition of galectin-3 mediated cellular interactions by pectic polysaccharides from dietary sources," Glycoconj J. 24(8):497-507.

Sato et al., (2008) Galectins as danger signals in host-pathogen and host-tumor interactions: new members of the growing group of "alarmins"? in Galectins, John Wiley & Sons; Eds: Klyosov AA, Zbigniew JW, Platt D. DOI:IO.1002/9780470378076.ch7, 115-145.

Scott-Burden et al., (1998) "Modulation of extracellular matrix by angiotensin ii: stimulated glycoconjugate synthesis and growth in vascular smooth muscle cells," J. of Cardiovascular Pharmacology. 16(Suppl. 4):S36-S41.

Shah et al., (2010) "Galectin-3, cardiac structure and function, and long-term mortality in patients with acutely decompensated heart failure," Eur J Heart Fail. DOI: 10.1093/eurjhf/hfq091: 826-832.

Shah et al. (2010) "Galectin-3, cardiac structure and function, and long-term mortality in patients with acute heart failure," J. Am. Coll. of Cardiol. 55(10A):A34.E329. (Presented at the American College of Cardiology Annual Scientific Session, 2010, Atlanta, GA).

Sherwi et al., (2010) "Does the severity of LV dysfunction or the extent of myocardial scar explain elevations in plasma galectin-3 in patients with heart failure," Eur. J. Heart Fail. Suppl. 9:S18.

Son et al., (2007) "Cardiomyocyte expression of PPARg leads to cardiac dysfunction in mice," The J. of Clinical Investigation, http://www.jci.org. 11 pages.

Stellbrink, (2007) "It's the metabolism, stupid! Why electrophysiologists should be interested in biomarkers of heart failure," Eur. Heart J. 28:1541-1542.

Tang et al., (2011) "Usefulness of plasma galectin-3 levels in systolic heart failure to predict renal insufficiency and survival," Am. J. Cardiol. 108(3):385-90.

Topol et al., (2001) "Single nucleotide polymorphisms in multiple novel thrombospondin genes may be associated with familial premature myocardial infarction," Circulation. 104:2641-2644.

Ueland et al., (2011) "Galectin-3 in heart failure: high levels are associated with all-cause mortality," Int. J. Cardiol. 150(3):361-4.

Mayo Clinic, Test ID: Gal3, Galectin-3, Serum. Web: http://mayomedicallaboratories.com/test-catalog/clinical+and+interpretive/86202. p. 1-2, Sep. 6, 2012.

bioMerieux: Cardiovascular Diseases: Prognosis in heart failure, Web: http://www.biomerieux-diagnostics.com/servlet/srt/bio/clincial-diagnostics/dynPage?open=CNL_HCP_CRD_PHF&doc=CNL_HCP_CRD_PHF_G_CHP_TXT_1&pubparams.sform=1&lang=en. pp. 1-2, Sep. 6, 2012.

Vasan et al., (2003) "Inflammatory markers and risk of heart failure in elderly subjects without prior myocardial infarction: the framingham heart study," Circulation. 107:1486-1491.

Wu et al., (2004) "The effect of diabetes on b-type natriuretic peptide concentrations in patients with acute dyspnea," Diabetes Care. 27(10):2398-2404.

Yanavitski and Givertz, (2011) "Novel biomarkers in acute heart failure," Curr. Heart Fail. Rep. 8(3):206-11.

Zhang et al., (2003) "The role of the Grb2-p38 MAPK signaling pathway in cardiac hypertrophy and fibrosis," J. Clinical Investigation. 111:833-841.

Zile et al. (2010) "Plasma galectin-3 levels in patients with structural and clinical manifestations of hypertensive heart disease: relationship to determinants of matrix composition," (Presented at the American Heart Association Scientific Sessions, 2010, Chicago, IL).

"BG Medicine Research Innovation Award," BG Medicine, <http://www.galectin-3.com/researchgrant/>.

Brott et al., (2011) "2011 ASA/ACCF/AHA/AANN/AANS/ACR/ASNR/CNS/SAIP/SCAI/SIR/SNIS/SVM/SVS Guideline on the management of patients with extracranial carotid and vertebral artery disease: executive summary," J Am Coll Cardiol. 57(8):1002-44.

"Galectin-3," BG Medicine, <http://www.galectin-3.com/home/about/galectin-3-inhibition/>, printed Nov. 7, 2012.

"Galectin-3," Laboratory Corporation of America, <https://www.labcorp.com/wps/portal/!ut/p/c1/04_SB8K8xLLM9MSSzPy8xBz9CP0os_hACzO_QCM_IwMLXyM3AyNjMycDU2dXQwN3M6B8JG55AwMCuv088nNT9QtyI8oBPK_DWA!!/dl2/d1/L0IDU0NTQ1FvS1VRIS9JSFJBQUInb0FNeUtibTZtL1ICSkp3NDU0a3N1eWx3ISEvN19VRTRTMUk5MzBPR1MyMEITM080TjJONjY4MC9zZWFyY2hCeUtleXdvcmQ!/?criterion=004110>, printed May 20, 2011.

Ho et al., (2012) "Galectin-3, a marker of cardiac fibrosis, predicts incident heart failure in the community," J. American College of Cardiology. (60)14:1249-56.

Saggiorato et al., (2001) "Galectin-3 as a presurgical immunocytodiagnostic marker of minimally invasive follicular thyroid carcinoma," J. Clin. Endo. & Met. 86(11):5152-5158.

Galectin-3 Human ELISA Kit (with color giving dyes) (ab119525); abcam®, <http://www.abcam.com/Galectin-3-Human-ELISA-kit-with-color-giving-dyes-ab119525.html>. 2 pages.

"Human Galectin-3 ELISA Kit," Aviscera Bioscience, <<http://www.aviscerabioscience.com/Product_Systems/Galectin-3/SK00199-01_avbs.pdf>>. 5 pages, Retrieved on Jan. 10, 2013.

"Human Galectin-3 ELISA Kit"; Catalog No. GWB-SKR226; GenWay Biotech Inc™, <<http://www.genwaybio.com/media/custom/upload/File-1345071780.pdf>>. 9 pages, Retrieved on Jan. 10, 2013.

Galectin-3 ELISA Kit (with color gving dyes), (av119525) ;* , <<http://www.ibl-america.com/pdf/newIBLelisa/27755.pdf>>. 2 pages, retrieved on Jan. 10, 2013.

"Human Galectin-3 ELISA"; Catalog No. KT-022; Kamiya Biomedical Company, <<http://www.kamiyabiomedical.com/pdf/KT-022.pdf>>. 13 pages, Retrieved on Jan. 10, 2013.

"Human Galectin-3 Immunoassay"; Catalog No. DGAL30; Quantikine®, <<http://www.funakoshi.co.jp/data/datasheet/RSD/DGAL30.pdf>>. 16 pages, Retrieved on Jan. 10, 2013.

Rabinovich et al., 2002. Role of galectins in inflammatory and immunomodulatory processes. Biochimica et Biophysica Acta 1572: 274-284.

Nangia-Makker et al., (2007) "Galectin-3 cleavage: a novel surrogate marker for matrix metalloproteinase activity in growing breast cancers," Cancer Res. 67(24):11760-11768.

Ochieng et al., (1994) "Galectin-3 is a novel substrate for human matrix metalloproteinases-2 and -9," Biochemistry. 33(47):14109-14.

Pelletier and Sato, (2002) "Specific recognition and cleavage of galectin-3 by Leishmania major through species-specific polygalactose epitope," J. Biological Chemistry. 277(20):17663-17670.

* cited by examiner

GALECTIN-3 IMMUNOASSAY

CROSS REFERENCE TO RELATED APPLICATIONS

This application is a continuation of U.S. patent application Ser. No. 16/444,402, filed Jun. 18, 2019, which is a continuation of U.S. patent application Ser. No. 15/424,306, filed Feb. 3, 2017, which is a continuation of U.S. patent application Ser. No. 12/608,821, filed Oct. 29, 2009, which claims the benefit of and priority of U.S. Provisional Patent Application No. 61/109,366, filed Oct. 29, 2008, the complete disclosure of each of which is incorporated by reference herein.

SEQUENCE LISTING

The instant application contains a Sequence Listing which has been submitted electronically in XML format and is hereby incorporated by reference in its entirety. Said XML copy, created on Dec. 6, 2023, is named BYG-029C3_SL.xml and is 11,931 bytes in size.

BACKGROUND OF THE INVENTION

Heart failure (HF) is a major public health problem in the United States. Approximately 5 million people suffer from the disease and the number of patients is steadily increasing. HF is a common but severe and complex clinical syndrome, especially among elderly people. HF refers to a condition in which the heart fails to pump enough blood to meet the body's needs. Insufficient pumping leads to the congestion of blood and other fluid in the liver, abdomen, lower extremities, and lungs. Thus, HF has also been called congestive heart failure (CHF), although the term HF is preferred because not all patients exhibit fluid congestion. HF results in a gradual deterioration of the patient often leading to cardiovascular mortality. Thus, a large number of patients die within one to five years after diagnosis. However, others may remain stable for prolonged periods. HF is a very different disease from heart ischemia caused by myocardial infarction or reperfusion injury.

Symptoms of HF include fatigue, weakness, rapid or irregular heartbeat, shortness of breath, persistent cough or wheezing, swelling of lower extremities or abdomen, sudden weight gain from fluid retention, lack of appetite or nausea, and chest pain. Currently, an important diagnostic test for HF is the comprehensive 2-dimensional echocardiogram together with Doppler flow studies to determine whether structural abnormalities exist. This test can determine the fraction of blood being pumped out of the ventricle (the ejection fraction, EF), which is an important measurement of heart function. The ejection fraction for a normal heart is approximately 60%. One or more of the following tests may also be used: radionuclide ventriculography, magnetic resonance imaging (MRI), a complete blood count, urinalysis, serum electrolytes, glycohemoglobin and blood lipids, tests of renal and hepatic function, tests of thyroid function, a chest radiograph, and a 12-lead electrocardiogram. Additionally, blood tests for biomarkers, such as B-type natriuretic peptide (BNP), can be performed. BNP is upregulated in response to the stretching of cardiomyocytes. Thus, a high level of BNP is indicative of a heart under stress, and is a good indicator of heart failure. However, other mechanisms that play a role in heart failure, such as inflammation, may not be reflected by an increase in BNP.

Early identification of patients at risk for developing HF may prevent rapid progression. Thus, it would be preferable to be able to identify those patients in whom heart failure is likely to occur before it actually does so. In addition, it would be preferable to be able to identify those patients suffering from heart failure who are at risk for developing severe complications or premature death.

Current methods can reliably exclude HF, but cannot reliably prove the existence of HF, nor can they predict the outcome of established HF. A need therefore exists for a simple and reliable method for predicting the likelihood of onset of HF symptoms and for assessing severity, stage of disease, and/or predicting the outcome of already established heart failure.

To find additional biochemical markers that reflect other mechanisms that play a role in heart failure, a microarray study was performed to determine which genes were upregulated in hypertensive rats that progressed to heart failure, compared to hypertensive rats that remained compensated (Schroen et al. (2004) *Circ. Res.* 95(5):515-22.). The gene most robustly upregulated in rats that progressed to heart failure was the beta-galactoside-binding lectin galectin-3. This finding was confirmed in a study by Sharma et al., which showed that high levels of galectin-3 are predictive for the development of heart failure in a rat model of hypertension (2004 *Circulation* 110(19):3121-8). This study further demonstrated the ability of exogenously applied galectin-3 to induce heart failure and excess collagen deposition. Recently, the concentration of galectin-3 in human plasma and serum was correlated with severity of HF, see International Patent Publication No. WO2005/040817, and corresponding U.S. patent application Ser. No. 10/575,745.

Galectins constitute a family of proteins characterized by their galactose-specific binding. All share common amino acid sequence in regions of their structure known as the carbohydrate recognition domain or CRD. Currently, 15 mammalian galectins have been identified. One subgroup contains galectins 1, 2, 5, 7, 10, 13, 14, and 15, each of which comprises a single CRD. A second subgroup contains a single species, galectin-3, which comprises a single CRD linked to an N-terminal domain comprising repeats of short amino acid sequences such as PGA. A third galectin subgroup contains galectins 4, 6, 8, 9, and 12, each of which comprises two CRDs joined by a linker of variable length. All of the galectins have significant amino acid sequence homology, and many appear in the human circulatory system.

Assays for galectin-3 exist, but none are suitable for routine clinical use. A suitable assay heretofore has eluded the art because of the complexity of galectin-3 as an analyte. It is difficult to specifically distinguish galectin-3 from other galectins in a sample, because galectin-3 shares a high degree of sequence similarity to the other 14 mammalian galectins, particularly in the conserved carbohydrate recognition domain (CRD). None of the other galectins has a known relation with HF. Another feature of galectin-3 that has hindered the development of a specific, reproducible detection assay is the propensity of galectin-3 to bind to various proteins, carbohydrates, nucleic acids and lipids. If an assay were developed that is industrially robust and sensitive and specific enough to quantitatively measure galectin-3 reproducibly in body fluids such as blood samples, the diagnosis and management of HF could be improved.

SUMMARY OF THE INVENTION

Methods for the detection of galectin-3 in clinical samples now have been identified and developed. It has now been discovered that the use of two binding moieties that bind specifically to at least two separate, non-overlapping epitopes on the N-terminus of galectin-3 can be used to produce various specific sandwich assay formats that can provide the reproducibility, specificity and sensitivity needed to diagnose and predict the outcome of subjects with HF. Accordingly, the present invention provides methods and kits for detecting the level of galectin-3 in a clinical sample. This permits improved management of the disease and provides diagnostic/prognostic information useful in its triage and management.

In one aspect, the invention relates to a kit for detecting the concentration of galectin-3 in a sample. The kit includes two binding moieties, e.g., monoclonal antibodies, at least one of which is labeled with a detectable label. The two binding moieties each bind respectively to spaced-apart epitopes on the N-terminal portion of galectin-3, which comprises the following 113 amino acid sequence:

```
                                      (SEQ ID NO: 1)
MADNFSLHDA LSGSGNPNPQ GWPGAWGNQP AGAGGYPGAS

YPGAYPGQAP PGAYPGQAPP GAYPGAPGAY PGAPAPGVYP

GPPSGPGAYP SSGQPSATGA YPATGPYGAP AGP
```

In one embodiment, the binding moieties respectively bind to an epitope defined by at least a portion of one of the following galectin-3 amino acid sequences: MADNFSLHDALS (SEQ ID NO: 3) (amino acids 1-12 of SEQ ID NO:1), MADNFSLHDALSGS (SEQ ID NO: 4) (amino acids 1-14 of SEQ ID NO:1), GNPNPQGWPGA (SEQ ID NO: 5) (amino acids 15-25 of SEQ ID NO:1), WGNQPAGAGG (SEQ ID NO: 6) (amino acids 26-35 of SEQ ID NO:1), YPGQAPPGAYPGQAPPGA (SEQ ID NO: 7) (amino acids 45-62 of SEQ ID NO:1), YPGAPGAYPGAPAPGV (SEQ ID NO: 8) (amino acids 63-78 of SEQ ID NO:1), YPGAPAPGVYPGPPSGPGA (SEQ ID NO: 9) (amino acids 70-88 of SEQ ID NO:1), YPSSGQPSATGA (SEQ ID NO: 10) (amino acids 89-100 of SEQ ID NO:1). While these depict linear epitopes, epitopes created by the secondary and tertiary structure of the N-terminus and comprising amino acids from spaced-apart sections of the sequence also may be used.

In another embodiment, the binding moieties used to detect galectin-3 are monoclonal antibodies, for example, M3/38, 9H3.2, and 87B5. M3/38 detects a linear epitope (YPGQAPPGAYPGQAPPGA (SEQ ID NO: 7) (amino acids 45-62 of SEQ ID NO:1)) on the N-terminus of galectin-3. M3/38 was prepared from the supernatant of the rat hybridoma M3/38.1.2.8 HL.2, a clone of which can be found in the American Type Culture Collection with ATCC® number TIB-166. 9H3.2 detects a linear epitope (MADNFSLHDALSGS (SEQ ID NO: 4) (amino acids 1-14 of SEQ ID NO:1)) at the extreme N-terminus of galectin-3. 9H3.2 is a mouse monoclonal IgG, affinity purified using protein A. 9H3.2 is available from Millipore (Millipore, 290 Concord Road, Billerica, MA 01821, USA), catalog no.: MAB4033. 87B5 detects a non-linear epitope comprising portions of GNPNPQGWPGA (SEQ ID NO: 5) (amino acids 15-25 of SEQ ID NO:1) and YPGAPAPGVYPGPPSGPGAYPSSGQPSATGA (SEQ ID NO: 11) (amino acids 70-100 of SEQ ID NO:1). 87B5 was prepared from the mouse-mouse hybridoma (X63-Ag8.653× BALB/c mouse spleen cells) clone 87B5, and is an IgG2a that was affinity purified using Protein A. 87B5 is available from Immuno-Biological Laboratories (IBL, 8201 Central Ave NE, Suite P, Minneapolis, MN 55432 USA)

In another aspect, the present invention relates to a method for detecting the level of human galectin-3 in a sample from a subject. The method includes subjecting the sample to a double binding moiety sandwich assay. In this method, at least one of the binding moieties is labeled with a detectable label and each of the binding moieties is specific for respective, non-overlapping epitopes on the N-terminal portion of galectin-3, such as those described above. In one embodiment, the detectable label is an enzyme or a fluorophore. The sandwich assay may provide a quantitative result or a qualitative result, for example, a result indicative of the presence or absence of a galectin-3 concentration above a threshold. The threshold may be in the range of, for example, 5-10 ng/ml, 10-15 ng/ml; 15-20 ng/ml; 20-25 ng/ml; 25-30 ng/ml; 30-35 ng/ml, or 35-40 ng/ml.

The method may include the additional step of comparing the result obtained in the assay to a data set relating the result to a galectin-3 concentration, e.g., a standard curve, to determine the concentration of galectin-3 in the sample, and then correlating the inferred concentration of galectin-3 with the risk that a subject is suffering from or at risk for developing HF, or to assess the stage or severity of the subject's HF. Of course, the result also may be directly correlated with the risk that a subject is suffering from or at risk for developing HF, or to assess the stage or severity of the subject's HF. The method may be repeated over time to obtain a trend. Additional variables may be considered such as, but not limited to, a subject's height, weight, age, sex, levels of other biomarkers, etc., to determine a subject's risk for developing HF, or to assess the stage of the subject's HF or its severity.

In another aspect, the present invention relates to a method for detecting a risk of development or progression of heart failure in a subject, including determining whether the galectin-3 concentration in a sample from the subject exceeds a threshold in the range of 15-20 ng/ml.

DESCRIPTION OF THE INVENTION

Definitions

Figure 1:
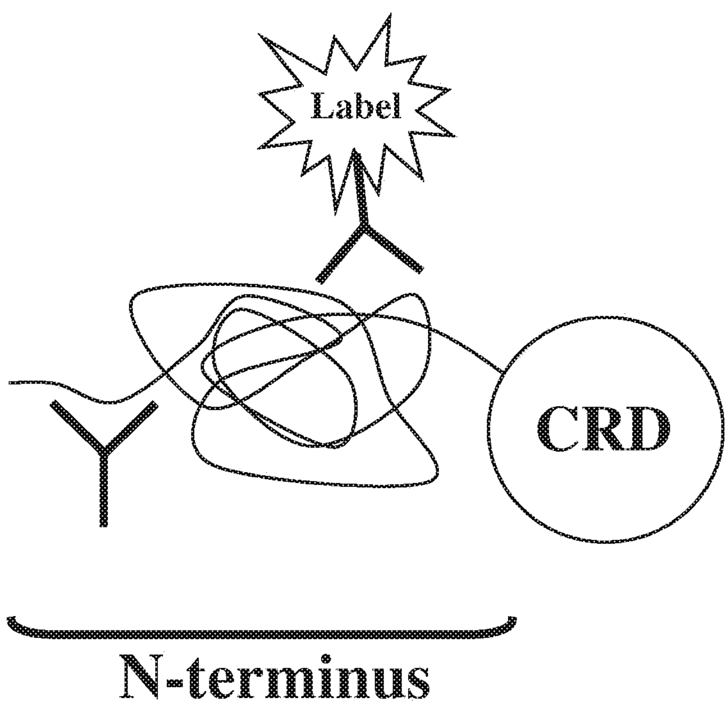
FIG. 1 is a cartoon drawing of a double monoclonal sandwich assay of the type exploited by the invention.

The terms "quantify" and "quantitate," as used herein, refer to the process of measuring the amount of galectin-3, or the relative amount of galectin-3, in a sample versus a standard or another sample (e.g., in terms of its concentration, mass, moles, or volume in a sample).

The terms "heart failure," "HF," "congestive heart failure, or "CHF" as used herein, refer to the complex clinical syndrome that impairs the ability of the ventricle to fill with or eject blood. Any structural or functional cardiac disorder can cause HF, with the majority of HF patients having impaired left ventricular (LV) myocardial function. Symptoms of HF include dyspnea (shortness of breath), fatigue, and fluid retention. The American Heart Association (AHA) has identified 4 stages in the development of HF. Patients in stages A and B show clear risk factors but have not yet developed HF. Patients in stages C and D currently exhibit or in the past have exhibited symptoms of HF. For example, Stage A patients are those with risk factors such as coronary artery disease, hypertension or diabetes mellitus who do not show impaired left ventricular (LV) function. Stage B patients are asymptomatic, but have cardiac structural abnormalities or remodeling, such as impaired LV function, hypertrophy or geometric chamber distortion. Stage C patients have cardiac abnormalities and are symptomatic. Stage D patients have refractory HF in which they exhibit symptoms despite maximal medical treatment. They are typically recurrently hospitalized or unable to leave the hospital without specialized intervention.

Galectin-3

Galectin-3 (GenBank Accession Nos.: NC_000014.7 (gene) and NP_002297.2 (protein)) is one of 15 mammalian beta galactoside-binding lectins, or "galectins," characterized by their galactose-specific binding. Galectin-3 has variously been referred to in the literature as LGALS3, MAC-2 antigen, Carbohydrate binding protein (CBP)-35, laminin binding protein, galactose-specific lectin 3, mL-34, L-29, hL-31, epsilon BP, and IgE-binding protein. Galectin-3 is composed of a carboxyl-terminal carbohydrate recognition domain (CRD) and amino-terminal tandem repeats (Liu, F.-T. (2000) Role of galectin-3 in inflammation. In *Lectins and Pathology*. M. Caron and D. Seve, eds. Harwood Academic Publishers, Amsterdam, The Netherlands, p. 51; Liu, F.-T. et al. (1995) *Am. J. Pathol.* 147:1016). Galectin-3 normally distributes in epithelia of many organs and various inflammatory cells, including macrophages as well as dendritic cells and Kupfer cells (Flotte, T. J. et al. (1983) *Am. J. Pathol.* 111:112).

Galectin-3 has been shown to play a role in a variety of cellular process, including cell-cell adhesion, cell-matrix interactions, phagocytosis, cell cycle, apoptosis, angiogenesis and mRNA splicing. Galectin-3 has been shown to function through both intracellular and extracellular actions (Sano, H. et al. (2000) *The Journal of Immunology,* 165: 2156-2164). It is a component of heterogeneous nuclear ribonuclear protein (hnRNP) (Laing, J. G. et al. (1998) *Biochemistry* 27:5329), a factor in pre-mRNA splicing (Dagher, S. F. et al. (1995) *Proc. Natl. Acad. Sci.* USA 92:1213) and has been found to control the cell cycle (Kim, H.-R. C. et al. (1999) *Cancer Res.* 59:4148) and prevent T-cell apoptosis through interaction with the Bcl-2 family members (Yang, R.-Y. et al. (1996) *Proc. Natl. Acad. Sci.* USA 93:6737). On the other hand, galectin-3, which is secreted from monocytes/macrophages (Sato, S. et al. (1994) *J. Biol. Chem.* 269:4424) and epithelial cells (Lindstedt, R. G. et al. (1993) *J. Biol. Chem.* 268:11750) has been demonstrated to function as an extracellular molecule in activating various types of cells such as monocytes/macrophages (Liu, F.-T. (1993) *Immunol Today* 14:486), mast cells, neutrophils and lymphocytes (Hsu, D. K., S. R. et al. (1996). *Am. J. Pathol.* 148:1661). Galectin-3 has been shown to act as a novel chemoattractant for monocytes and macrophages (Sano, H. et al. (2000) *The Journal of Immunology,* 2000, 165:2156-2164). Galectin-3 has been implicated in diseases and conditions such as cancer, inflammation, and heart failure. As disclosed in International Patent Publication No. WO2005/040817, quantitation of galectin-3 is particularly suitable for use in an assay to diagnose and detect the severity of HF and to predict outcome.

Unlike the other mammalian galectins, galectin-3 comprises an atypical N-terminal domain, comprising the amino acid sequence:

```
                                        (SEQ ID NO: 1)
MADNFSLHDA LSGSGNPNPQ GWPGAWGNQP AGAGGYPGAS

YPGAYPGQAP PGAYPGQAPP GAYPGAPGAY PGAPAPGVYP

GPPSGPGAYP SSGQPSATGA YPATGPYGAP AGP.
```

As can be appreciated from an inspection, the sequences of the N-terminus of galectin-3 are dissimilar to sequences of other mammalian galectins but comprise multiple repeats of the type PGAYPG$(X)_{1-4}$ (SEQ ID NO:2), with intervening proline-, glycine-, and tyrosine-rich regions. The existence of repeated sequences in the N-terminal domain decreases the number of different potential epitopes specific to galectin-3, complicating the development of a detection assay. However, it has now been discovered that N-terminal epitopes can reliably distinguish galectin-3 from other mammalian galectins. Using the assays disclosed herein it is possible to correlate reliably and reproducibly galectin-3 clinical results with the presence, severity and stage of progression of HF in a subject. Exemplary N-terminal epitopes include, but are not limited to, MADNFSLHDALS (SEQ ID NO: 3) (amino acids 1-12 of SEQ ID NO:1), MADNFSLHDALSGS (SEQ ID NO: 4) (amino acids 1-14 of SEQ ID NO:1), GNPNPQGWPGA (SEQ ID NO: 5) (amino acids 15-25 of SEQ ID NO:1), WGNQPAGAGG (SEQ ID NO: 6) (amino acids 26-35 of SEQ ID NO:1), YPGQAPPGAYPGQAPPGA (SEQ ID NO: 7) (amino acids 45-62 of SEQ ID NO:1), YPGAPGAYPGAPAPGV (SEQ ID NO: 8) (amino acids 63-78 of SEQ ID NO:1), YPGAPAPGVYPGPPSGPGA (SEQ ID NO: 9) (amino acids 70-88 of SEQ ID NO:1), YPSSGQPSATGA (SEQ ID NO: 10) (amino acids 89-100 of SEQ ID NO:1), where the letters represent standard amino acid code. Other epitopes appear on the N-terminus comprising amino acids spaced apart on the primary structure but presented together in the tertiary structure, and these also can be addressed by the binders used in the assays of the invention.

Detection of Galectin-3 by Sandwich Assay

According to the methods of the invention, the concentration of galectin-3 may be quantitated in a bodily fluid sample using a pair of binding moieties that bind specifically to N-terminal portions of galectin-3. A "binding moiety" refers to a molecule that binds or interacts selectively or preferentially with a polypeptide or peptide. Examples of binding moieties include, but are not limited to, proteins, such as antibodies, galectin binding protein (GBP) interaction fusion protein, peptide aptamers, avimers, Fabs, sFvs, Adnectins and Affibody® ligands; nucleic acids, such as DNA and RNA (including nucleotide aptamers), and lipids, such as membrane lipids.

The methods and compositions of the present invention can be used to detect the concentration of galectin-3 in a clinical sample, such as serum, for the diagnosis of HF. According to the methods of the invention, the test sample used in the detection of galectin-3 can be any body fluid or tissue sample, including, but not limited to, whole blood, serum, plasma, or lymph, and less preferably urine, gastric juices, bile, saliva, sweat, and spinal fluids, stool, or muscle biopsy. In a preferred embodiment, the sample is a blood sample. In another embodiment, the sample is a plasma sample. Serum samples may also be used. Furthermore, the body fluids may be either processed (e.g., serum) or unprocessed. Methods of obtaining a body fluid from a subject are known to those skilled in the art.

According to the methods of the invention, galectin-3 is detected and quantified using a "sandwich" assay. In this embodiment, two molecules ("binding moieties") such as monoclonal antibodies that specifically bind to non-overlapping sites ("epitopes") on the N-terminus of galectin-3 are used. See FIG. 1. Typically, one binding moiety is immobilized on a solid surface where it binds with and captures galectin-3. This first binding moiety is therefore also referred to herein as the capture binding moiety. A second binding moiety is detectably labeled, for example, with a fluorophore, enzyme, or colored particle, such that binding of the second binding moiety to the galectin-3-complex indicates that galectin-3 has been captured. The intensity of the signal is proportional to the concentration of galectin-3 in the sample. The second binding moiety is therefore also referred to herein as the detection binding moiety or label binding moiety. A binding moiety can be any type of molecule, as long as it specifically binds to a portion of the N-terminus of galectin-3. In a preferred embodiment, the binding moieties used are monoclonal anti-galectin-3 antibodies, i.e., monoclonals raised against or otherwise selected to bind to separate portions of the N-terminal 113 amino acids of galectin-3.

Such assay procedures can be referred to as two-site immunometric assay methods, "sandwich" methods or (when antibodies are the binders) "sandwich immunoassays." As is known in the art, the capture and detection antibodies can be contacted with the test sample simultaneously or sequentially. Sequential methods, sometimes referred to as the "forward" method, can be accomplished by incubating the capture antibody with the sample, and adding the labeled detection antibody at a predetermined time thereafter. Alternatively, the labeled detection antibody can be incubated with the sample first and then the sample can be exposed to the capture antibody (sometimes referred to as the "reverse" method). After any necessary incubation(s), which may be of short duration, the label is detected and may also be measured. Such assays may be implemented in many specific formats known to those of skill in the art, including through use of various high throughput clinical laboratory analyzers or with point of care or home testing devices.

In one embodiment, a lateral flow device may be used in the sandwich format, wherein the presence of galectin-3 above a baseline sensitivity level in a biological sample will permit formation of a sandwich interaction upstream of or at the capture zone in the lateral flow assay. See, for example, U.S. Pat. No. 6,485,982. The capture zone as used herein may contain capture binding moieties such as antibody molecules, suitable for capturing galectin-3, or immobilized avidin or the like for capture of a biotinylated complex. See, for example, U.S. Pat. No. 6,319,676. The device may also incorporate a luminescent label suitable for capture in the capture zone, the concentration of galectin 3 being proportional to the intensity of the signal at the capture site. Suitable labels include fluorescent labels immobilized on polystyrene microspheres. Colored particles also may be used.

Other assay formats that may be used in the methods of the invention include, but are not limited to, flow-through devices. See, for example, U.S. Pat. No. 4,632,901. In a flow-through assay, one binding moiety (for example, an antibody) is immobilized to a defined area on a membrane surface. This membrane is then overlaid on an absorbent layer that acts as a reservoir to pump sample volume through the device. Following immobilization, the remaining protein-binding sites on the membrane are blocked to minimize non-specific interactions. In operation, a biological sample is added to the membrane and filters through, allowing any analyte specific to the antibody in the sample to bind to the immobilized antibody. In a second step, a labeled secondary antibody may be added or released that reacts with captured marker to complete the sandwich. Alternatively, the secondary antibody can be mixed with the sample and added in a single step. If galectin-3 is present, a colored spot develops on the surface of the membrane.

The most common enzyme immunoassay is the "Enzyme-Linked Immunosorbent Assay (ELISA)." ELISA is a technique for detecting and measuring the concentration of an antigen using a labeled (e.g., enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984), *J. Clin. Chem. Clin. Biochem.* 22:895-904.

In a "sandwich ELISA," an antibody (e.g., anti-galectin-3) is linked to a solid phase (i.e., a microtiter plate) and exposed to a biological sample containing antigen (e.g., galectin-3). The solid phase is then washed to remove unbound antigen. A labeled antibody (e.g., enzyme linked) is then bound to the bound antigen, forming an antibody-antigen-antibody sandwich. Examples of enzymes that can be linked to the antibody are alkaline phosphatase, horseradish peroxidase, luciferase, urease, and β-galactosidase. The enzyme-linked antibody reacts with a substrate to generate a colored reaction product that can be measured. This measurement can be used to derive the concentration of galectin-3 present in a sample, for example, by comparing the measurement to a galectin-3 standard curve. Galectin-3 concentration in a sample from a subject may be determined to be above or below a threshold. The threshold may be in the range of, for example, 5-10 ng/ml, 10-15 ng/ml; 15-20 ng/ml; 20-25 ng/ml; 25-30 ng/ml; 30-35 ng/ml, or 35-40 ng/ml.

Any of the immunoassays described herein suitable for use with the kits and methods of the present invention can also use any binding moiety in the place of an antibody.

Binding Moieties

In a preferred embodiment of the invention, anti-galectin-3 antibodies, preferably monoclonal antibodies, are used as binding moieties.

Monoclonal Antibodies

In preferred embodiments of the invention, monoclonal antibodies are used. A monoclonal antibody refers to an antibody that is derived from a single clone, including any eukaryotic, prokaryotic, or phage clone. The monoclonal antibody may comprise, or consist of, two proteins, i.e., heavy and light chains. The monoclonal antibody can be prepared using one of a wide variety of techniques known in the art including the use of hybridoma, recombinant, and phage display technologies, or a combination thereof.

Anti-galectin-3 monoclonal antibodies may be prepared using any known methodology, including the seminal hybridoma methods, such as those described by Kohler and Milstein (1975), *Nature*. 256:495. In a hybridoma method, a mouse, hamster, or other appropriate host animal is immunized with an immunizing agent to elicit lymphocytes that produce or are capable of producing antibodies that will specifically bind to the immunizing agent. Alternatively, the lymphocytes may be immunized in vitro.

The immunizing agent will typically include at least a portion of the galectin-3 polypeptide or a fusion protein thereof. For example, synthetic polypeptide or recombinant polypeptide comprising any galectin-3 N-terminal epitopes may be used as an immunizing agent. Exemplary N-terminal epitopes include, but are not limited to, MADNFSLHDALS (SEQ ID NO: 3) (amino acids 1-12 of SEQ ID NO:1), MADNFSLHDALSGS (SEQ ID NO: 4) (amino acids 1-14 of SEQ ID NO:1), GNPNPQGWPGA (SEQ ID NO: 5) (amino acids 15-25 of SEQ ID NO:1), WGNQPAGAGG (SEQ ID NO: 6) (amino acids 26-35 of SEQ ID NO:1), YPGQAPPGAYPGQAPPGA (SEQ ID NO: 7) (amino acids 45-62 of SEQ ID NO:1), YPGAPGAYPGAPAPGV (SEQ ID NO: 8) (amino acids 63-78 of SEQ ID NO:1), YPGAPAPGVYPGPPSGPGA (SEQ ID NO: 9) (amino acids 70-88 of SEQ ID NO:1), YPSSGQPSATGA (SEQ ID NO: 10) (amino acids 89-100 of SEQ ID NO:1). A fusion protein may be made by fusing a polypeptide to a carrier protein, for example, keyhole limpet hemocyanin (KLH, EMD Biosciences, San Diego, Calif), BSA (EMD Biosciences, San Diego, Calif.), or ovalbumin (Pierce, Rockford, Ill.). The immunizing agent may be administered to a mammal with or without adjuvant according to any of a variety of standard methods. The immunizing agent may be administered only once, but is preferably administered more than once according to standard boosting schedules.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell population which is screened for species having appropriate specificity and affinity to epitopes on the N-terminal portion of galectin-3 (Goding, (1986) Monoclonal Antibodies: Principles and Practice, Academic Press, pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies (Kozbor, J. (1984) *Immunol.,* 133:3001; Brodeur et al., *Monoclonal Antibody Production* Techniques and Applications, Marcel Dekker, Inc., New York, (1987) pp. 51-63).

The culture medium in which the hybridoma cells are cultured can then be assayed for the presence of monoclonal antibodies directed against the N-terminus of galectin-3, e.g., by screening with a labeled galectin-3 N-terminal polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980), *Anal. Biochem.,* 107:220. Various analysis protocols to determine binding specificity are available commercially as kits or as a service.

Monoclonal antibodies also may be made by recombinant DNA methods, such as those described in U.S. Pat. No. 4,816,567. DNA encoding suitable monoclonal antibodies can be isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., (1984) *Proc. Natl. Acad. Sci.* USA, 81:6851) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies can also be produced using phage display libraries (Hoogenboom and Winter (1991), *J. Mol. Biol.* 227:381; Marks et al. (1991), *J. Mol. Biol.,* 222:581). The techniques of Cole et al. and Boerner et al. are also available for the preparation of monoclonal antibodies (Cole et al. (1985), Monoclonal Antibodies and Cancer Therapy, Alan R. Liss, p. 77 and Boerner et al. (1991), *J. Immunol.,* 147(1):86-95). Similarly, antibodies can be made by introducing of immunoglobulin loci into transgenic animals, e.g., mice in which the endogenous immunoglobulin genes have been partially or completely inactivated.

The antibodies may also be affinity matured using known selection and/or mutagenesis methods as described above. Preferred affinity matured antibodies have an affinity which is five times, more preferably 10 times, even more preferably 20 or 30 times greater than the starting antibody from which the matured antibody is prepared. In a particularly preferred embodiment, the antibodies used to detect galectin-3 are monoclonal antibodies, for example, M3/38, 9H3.2, and 87B5. M3/38 detects a linear epitope (YPGQAPPGAYPGQAPPGA (SEQ ID NO: 7) (amino acids 45-62 of SEQ ID NO:1)) on the N-terminus of galectin-3. M3/38 was prepared from the supernatant of the rat hybridoma M3/38.1.2.8 HL.2, a clone of which can be found in the American Type Culture Collection with ATCC® number TIB-166. 9H3.2 detects a linear epitope (MADNFSLHDALSGS (SEQ ID NO: 4) (amino acids 1-14 of SEQ ID NO:1) at the extreme N-terminus of galectin-3. 9H3.2 is a mouse monoclonal IgG, affinity purified using protein A. 9H3.2 is available from Millipore (Millipore, 290 Concord Road, Billerica, MA 01821, USA), catalog no.: MAB4033. 87B5 detects a non-linear epitope comprising portions of GNPNPQGWPGA (SEQ ID NO: 5) (amino acids 15-25 of SEQ ID NO:1) and YPGAPAPGVYPGPPSGPGAYPSSGQPSATGA (SEQ ID NO: 11) (amino acids 70-100 of SEQ ID NO:1). 87B5 was prepared from the mouse-mouse hybridoma (X63-Ag8.653× BALB/c mouse spleen cells) clone 87B5, and is an IgG2a that was affinity purified using Protein A. 87B5 is available from Immuno-Biological Laboratories (IBL, 8201 Central Ave NE, Suite P, Minneapolis, MN 55432 USA).

In a currently preferred embodiment, the capture binding moiety is the anti-galectin-3 monoclonal antibody, M3/38 and the labeled detection binding moiety is a second anti-galectin-3 monoclonal antibody, 87B5. The given designations for these antibodies are not limiting. In another embodiment, the capture antibody is 9H3.2 and the labeled detection binding moiety is M3/38. Other antibodies which recognize the epitopes described above also may be used.

Other binding moieties may be used with the methods and kits of the present invention. Examples of binding moieties include, but are not limited to, proteins, peptide aptamers, avimers, Adnectins and Affibody® ligands; nucleic acids, such as DNA and RNA (including nucleotide aptamers), and lipids, such as membrane lipids.

Aptamers

Nucleotide aptamers are small peptides or small nucleotide sequences that bind with high affinity to a target of choice. Nucleotide aptamers are produced by a selection process called Systematic Evolution of Ligands by Exponential Enrichment (SELEX), also referred to as in vitro selection or in vitro evolution. In this procedure, a target molecule is exposed to a large, randomly generated oligonucleotide library. The unbound oligonucleotides are separated out of the mixture by any number of methods, usually affinity chromatography. The oligonucleotides that remain bound are eluted and amplified. The target molecule is then exposed to the newly-synthesized oligonucleotides, and the selection process is repeated for several rounds with increasingly stringent conditions to separate out unbound sequences. The resulting oligonucleotides are then sequenced to determine their identity. See U.S. patent application Ser. No. 07/536,428; U.S. Pat. Nos. 5,475,096; and 5,270,163.

Peptide aptamers typically consist of a short variable peptide domain. Peptide aptamers comprise a variable peptide loop attached at both ends to a protein scaffold. This double structural constraint greatly increases the binding affinity of the peptide aptamer to levels comparable to an antibody's (nanomolar range). The variable loop length is typically 10 to 20 amino acids, and the scaffold may be any protein that is soluble and compact, such as the bacterial protein thioredoxin A. A variable loop can be inserted within the reducing active site of thioredoxin A, which is a -Cys-Gly-Pro-Cys- (SEQ ID NO: 12) loop in the wild protein, the two cysteine lateral chains being able to form a disulfide bridge. Peptide aptamer selection can be made using different systems, such as the yeast two-hybrid system. For further discussion of peptide aptamers, see International Patent Publication No. WO2007/117657.

Avimers

An avimer (avidity multimer) is a short peptide sequence that contains multiple regions of low affinity to a target. The presence of multiple unique regions of low affinity act together to produce a high affinity binding moiety. Small size and high disulfide density contribute to the low immunogenicity of avimers. To identify avimers with high binding affinity for a protein of interest, a highly diverse pool of monomers is created by synthetic recombination. This pool of monomers can be screened against a target protein using phage display or another preferred screening method. Once candidates are found, another monomer is added and the new library of dimers is screened against the target. After iteration, a trimer with very high binding affinity for its target protein is isolated (see Silverman et al. (2005), *Nature Biotechnology* 23, 1556-1561).

Adnectins

An Adnectin consists of a backbone of the natural amino acid sequence of a certain domain of human fibronectin and one to three targeting loops which contain randomized sequence. Adnectins are screened and isolated based on ability to specifically recognize a therapeutic target of interest (see, for example, U.S. Pat. No. 6,818,418).

Affibody® Ligands

Affibody® ligands are small peptides comprised of a "scaffold" domain and a variable domain. The "scaffold" domain comprises a non-cysteine three-helix bundle domain, a structure based on staphylococcal protein A. The variable domain contains randomly-generated sequences which can be screened against a target of interest. Libraries of Affibody® ligands are constructed, and the libraries can be screened to find candidates with high binding affinity to a protein of interest. See Nygren, P.-Å. (2008) *FEBS Journal* 275, 2668-2676.

Naturally-Occuring Binding Partners

Naturally-occurring galectin-3 binding partners that bind to the N-terminus of galectin-3 can be isolated or produced recombinantly and used as binding moieties. Galectin-3 binding partners or fragments thereof can be used as either capture or detection binding moieties, depending upon the particular constraints of the assay. Examples of galectin-3 binding partners include, but are not limited to mycolic acids and lipopolysaccharides (Barboni et al. (2005) *FEBS Letters* 579:6749-6755). Additionally, circulating galectin-3 triggers an auto-immune response resulting in the generation of auto-antibodies against galectin-3 in serum under both normal and pathological conditions (Jensen-Jarolim et al. (2001) *J Clin Immunol.* 21(5):348-56; Lim et al., (2002) Biochem Biophys Res Commun. 295(1):119-24; Mathews et al. (1995) *J Clin Immunol.* 15(6):329-37). These autoantibodies appear to target against epitopes on the N-terminal domain of galectin-3 (Mathews et al., supra).

Capture

The important property of the capture binding moiety is that it provides a means of separation from the remainder of the test mixture. Accordingly, as is understood in the art, the capture binding moiety can be introduced to the assay in an already immobilized or insoluble form, that is, a form which enables separation of the complex from the remainder of the test solution. Alternatively, immobilization may be done by capture of an immune complex comprising galectin-3 subsequent to introduction of a soluble form of the capture binding moiety to the sample. Examples of immobilized capture binding moieties are binding moieties covalently or noncovalently attached to a solid phase such as a magnetic particle, a latex particle, a microtiter plate well, a membrane, a chip, a bead, a cuvette, an array, or other reaction vessel or holder. Examples of a soluble capture binding moiety is a binding moiety which has been chemically modified with a ligand, e.g., a hapten, biotin, or the like, and which acts as a hook to permit selective capture of complex including galectin-3. Methods of coupling the capture binding moiety to a solid phase are well known in the art. These methods can employ bifunctional linking agents, for example, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations.

Labels

According to the methods of the invention, the label used can be selected from any of those known conventionally in the art. Preferred labels are those that permit more precise quantitation. Examples of labels include but are not limited to a fluorescent moiety, an enzyme, an electrochemically active species, a radioactive isotope, a chemiluminescent molecule, a latex or gold particle, a detectable ligand (e.g., detectable by secondary binding of a labeled binding partner for the ligand), etc. In a preferred embodiment, the label is an enzyme or a fluorescent molecule. Methods for affixing the label to the binding moiety are well known in the art, and include covalent and non-covalent linkage.

In one embodiment, a binding moiety can be labeled with a fluorescent compound. When the fluorescently labeled binding moiety is exposed to light of the proper wavelength, its presence can then be detected by the fluorescence emitted. Among the most commonly used fluorescent labeling compounds are Cy3 and Cy5 (water-soluble fluorescent dyes of the cyanine dye family- "Cy" dyes), fluorescein isothiocyanate, rhodamine, phycoerytherin, phycocyanin, allophycocyanin, o-phthalaldehyde and fluorescamine.

In another embodiment, the detection binding moiety is detectably labeled by linking the binding moiety to an enzyme. The enzyme, in turn, when exposed to its substrate, will react with the substrate in such a manner as to produce a chemical moiety which can be detected, for example, by spectrophotometric, fluorometric or visual means. Enzymes which can be used to detectably label the binding moieties of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may also be accomplished using a radioactively labeled binding moiety. It is then possible to detect the binding moiety through the use of radioimmune assays. The radioactive isotope can be detected by such means as the use of a gamma counter or a scintillation counter or by audoradiography. Isotopes which are particularly useful for the purpose of the present invention are $^{3}H$, $^{131}I$, $^{35}S$, $^{14}C$, and preferably $^{125}I$.

A binding moiety also can be detectably labeled by coupling it to a chemiluminescent compound. The presence of the chemiluminescent-binding moiety is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

Alternate Forms of Galectin-3

Galectin-3 may exist in a sample in a plurality of different forms characterized by detectably different masses. These forms can result from pre-translational modifications, post-translational modifications or both. Pre-translational modified forms include allelic variants, splice variants, and RNA-editing forms. Post-translationally modified forms include forms resulting from, among other things, proteolytic cleavage (e.g., fragments of a parent protein), complexation, glycosylation, phosphorylation, lipidation, oxidation, methylation, cystinylation, sulphonation and acetylation. Modified forms of galectin-3, as long as they retain the relevant N-terminal epitopes, may be detected according to the methods of the present invention.

Diagnostic and Prognostic Uses

The galectin-3 assay of the invention can be used to identify subjects at risk for developing or to identify subjects suffering from HF. In this method, patients or other subjects with an identified risk of developing HF may be monitored for changes in galectin-3 levels quantitated from a body fluid over time using an immunoassay of the invention. In certain embodiments, a subject with an identified risk to develop HF may monitor his or her galectin-3 levels over time, for example, monthly, quarterly, bi-yearly, yearly, every 2 years, or every 5 years.

In another embodiment, galectin-3 may be used as a diagnostic marker to determine the presence, stage or severity of HF in a subject or to predict his or her prognosis by measuring the concentration of galectin-3 in a sample and comparing this result to data correlating galectin-3 concentration with severity or stage of HF disease of human subjects. Methods of diagnosis and/or predicting prognosis described herein may be combined with other methods for diagnosis and/or predicting prognosis commonly used in the art, such as echocardiograms with Doppler analysis, radionuclide ventriculography, magnetic resonance imaging (MRI), a complete blood count, urinalysis, serum electrolytes, glycohemoglobin and blood lipids, tests of renal and hepatic function, tests of thyroid function, a chest radiograph, a 12-lead electrocardiogram, blood tests for biomarkers such as BNP, etc.

Other Uses

The methods and kits of the present invention are also suitable for use in detecting other conditions characterized by an increased or decreased concentration of galectin-3. The expression of this galectin-3 is up-regulated during inflammation (Flotte et al. (1983) *Am. J. Pathol.* 111:112.), cell proliferation (Agrwal, et al. (1999) *J. Biol. Chem.* 264:17236) and cell differentiation (Nangia-Makker et al. (1993). *Cancer Res.* 53:1) and through transactivation by viral proteins (Hsu, D. et al. (1996) *Am. J. Pathol.* 148:

1661). Its expression is also affected by neoplastic transformation. For example, galectin-3 upregulation is found in certain types of lymphomas (Hsu, D. et al. (1996) *Am. J. Pathol.* 148:1661), and thyroid carcinoma (Fernadez, P. L. et al. (1997) *J. Pathol.* 181:80), while galectin-3 is down-regulated in other types of malignancies such as colon (Lotz, M. M. et al. (1993) *Proc. Natl. Acad. Sci. USA* 90:3466), breast (Castronovo, V., F. A. et al. (1996) *J. Pathol.* 179:43.), ovarian (Van den Brüle, F. A. et al. (1994) *Eur. J. Cancer* 30A:1096) and uterine (Van den Brüle, F. A. et al. (1996) *Hum. Pathol.* 27:1185) carcinomas. The expression of galectin-3 has a strong correlation with the grade and malignant potential of primary brain tumors (Bresalier, R. et al. (1997). *Cancer* 80:776).

Galectin-3 plays a role in many other diseases, conditions and disorders, including autoimmune disorders and vascular complications in diabetes and hypertension. Galectin-3 has been detected in tissues affected by inflammatory diseases. For example, galectin-3 was detected in the tears of patients with inflammatory ocular diseases (Hrdlickova-Cela et al. (2001), *Br J Ophthalmol,* 85:1336-40). Increased galectin-3 levels have also been noted in human atherosclerotic lesions (Ohshima et al. (2003), *Arthritis Rheum,* 48:2788-95; Nachtigal et al. (1998), *Am J Pathol,* 152:1199-208).

Kits

The invention also provides a kit for quantitating galectin-3 useful in detecting an increased risk of HF, diagnosing presence of HF, determining severity of HF, or predicting prognosis of a subject with HF. The kit may comprise one or more binding moieties for quantitating the level of galectin-3 in a bodily fluid. For example, a kit can comprise capture and detection binding moieties that specifically recognize epitopes on the N-terminus of galectin-3. The capture and detection binding moieties may comprise an antibody that is immunospecific for galectin-3. In one embodiment, the kit comprises two anti-galectin-3 monoclonal antibodies, e.g., M3/38, 9H3.2, or 87B5. Capture binding moieties present in a kit may be pre-attached to a solid surface, for example, but not limited to, a plastic or glass container or slide. A kit may further comprise containers for mixing the sample with the binding moieties. Such containers may be suitable for use with a detection apparatus capable of detecting the signal produced by the detection binding moiety. The kit may further comprise one or more reagents (e.g., a different antibody) for measuring the level of a second marker indicative of the same disease.

A kit of the invention may additionally comprise one or more of the following: (1) instructions for using the kit for determining the level of galectin-3; (2) a labeled binding partner to any antibody present in the kit; (3) a solid phase (such as a reagent strip) upon which any such antibody is immobilized; and (4) a label or insert indicating regulatory approval for diagnostic, prognostic, or therapeutic use or any combination thereof. If a labeled binding partner to the antibody is not provided, the antibody itself can be labeled with a detectable marker, e.g., a chemiluminescent, enzymatic, fluorescent, or radioactive moiety.

EXAMPLES

The invention is further illustrated by the following examples. The examples are provided for illustrative purposes only, and are not to be construed as limiting the scope or content of the invention in any way.

Example 1: Enzyme-Linked Immunosorbent Assay for Quantitative Detection of Human Galectin-3

The human galectin-3 ELISA is an enzyme-linked immunosorbent assay for the quantitative detection of human galectin-3 in EDTA plasma. Human galectin-3 present in the sample or standard bound to antibodies adsorbed to the microwells. Following incubation unbound material was removed during a wash step. HRP conjugated to anti-human galectin-3 antibody was added and bound to the galectin-3 captured by the coating antibody. Following incubation unbound HRP-conjugate was removed during a wash step, and substrate solution reactive with HRP was added to the wells. A colored product was formed in proportion to the amount of human galectin-3 present in the sample or standard. The reaction was terminated by addition of acid and absorbance was measured at 450 nm. A standard curve was prepared from 7 human galectin-3 standard dilutions and human galectin-3 sample concentration determined. Plasma was removed from the clot or cells as soon as possible after clotting and separation of the blood sample. Samples containing a visible precipitate were clarified prior to use in the assay. Grossly hemolyzed or lipemic specimens were not used. Samples were aliquoted and stored frozen at −20° C. to avoid loss of bioactive human galectin-3. Prior to assay, frozen samples were brought to room temperature slowly and mixed gently.

The following reagents were prepared for use in the assay. Wash Buffer (1×) was prepared by mixing 50 ml of Wash Buffer Concentrate (20×, PBS with 1% Tween 20) into a clean 1000 ml graduated cylinder. The final volume was brought to 1000 ml with deionized water and the solution was gently mixed. The pH of the final solution was adjusted to 7.4. Wash Buffer (1×) was transferred to a clean wash bottle.

Assay Buffer was prepared by adding 5 ml of Assay Buffer Concentrate (20×, PBS with 1% Tween 20 and 10% BSA) into a clean 100 ml graduated cylinder. The final volume was brought to 100 ml with deionized water and the solution was gently mixed.

A concentrated HRP-Conjugate solution was diluted 1:100 ratio in Assay Buffer (1×) in a clean plastic tube. Human galectin-3 standard was diluted to 60 ng/ml by addition of distilled water, and the mixture was gently swirled to ensure complete and homogeneous solubilization. The reconstituted standard was allowed to sit for 10 minutes prior to dilutions being made.

To make an external standard dilution, 7 tubes were labeled (S1, S2, S3, S4, S5, S6, S7), one for each standard point. Serial dilutions were prepared at a ratio of 1:2 as follows: 225 μl of Sample Diluent was pipetted into each tube. 225 μl of reconstituted standard (concentration=60 ng/ml) was pipetted into the first tube, labeled 51, and mixed (concentration of standard 1=30 ng/ml). 225 μl of this dilution was pipetted into the second tube, labeled S2, and mixed thoroughly before the next transfer. This serial dilution was repeated 5 more times to create the points of the standard curve. The Sample Diluent served as the blank.

Lyophilized human galectin-3 was reconstituted in distilled water to the following volumes: High Control (180 μl, 56-84 ng/ml), Medium Control (200 μl, 32-48 ng/ml), and Low Control (130 μl, 3.4-5.8 ng/ml). Vials were swirled to ensure quantitative solubilization of contents. The reconstituted controls were allowed to sit for 10 minutes.

Each sample, standard, blank and optional control sample should be assayed in duplicate. Microwell strips were washed twice with approximately 400 μl Wash Buffer per well with thorough aspiration of microwell contents between washes. The Wash Buffer was allowed to sit in the wells for about 10-15 seconds before aspiration.

After the last wash step, the wells were emptied and the microwell strips were tapped on absorbent paper to remove excess Wash Buffer. The microwell strips were not allowed to dry.

100 μl of the standards (S1-S7) were pipetted in the standard wells according to Table 1.

TABLE 1

Table depicting an example of the arrangement of blanks, standards and samples in the microwell strips:

| | 1 | 2 | 3 | 4 |
|---|---|---|---|---|
| A | Standard 1 (30.00 ng/ml) | Standard 1 (30.00 ng/ml) | Sample 1 | Sample 1 |
| B | Standard 2 (15.00 ng/ml) | Standard 2 (15.00 ng/ml) | Sample 2 | Sample 2 |
| C | Standard 3 (7.5 ng/ml) | Standard 3 (7.5 ng/ml) | Sample 3 | Sample 3 |
| D | Standard 4 (3.75 ng/ml) | Standard 4 (3.75 ng/ml) | Sample 4 | Sample 4 |
| E | Standard 5 (1.88 ng/ml) | Standard 5 (1.88 ng/ml) | Sample 5 | Sample 5 |
| F | Standard 6 (0.94 ng/ml) | Standard 6 (0.94 ng/ml) | Sample 6 | Sample 6 |
| G | Standard 7 (0.47 ng/ml) | Standard 7 (0.47 ng/ml) | Sample 7 | Sample 7 |
| H | Blank | Blank | Sample 8 | Sample 8 |

100 μl of Sample Diluent were added in duplicate to the blank wells. 80 μl of Sample Diluent was added to the sample wells. 20 μl of each sample was added in duplicate to the sample wells. Wells were covered with an adhesive film and incubated at room temperature (18 to 25° C.) for 1 hour on a microplate shaker set at 200 rpm. The adhesive film was removed and the wells emptied. The microwell strips were washed 3 times as above.

Next, 100 μl of diluted HRP-Conjugate were added to all wells, including the blank wells. Wells were covered with an adhesive film and incubated at room temperature (18 to 25° C.) for 1 hour on a microplate shaker set at 200 rpm. The adhesive film was removed and the wells emptied. Microwell strips were washed 3 times as above.

Then, 100 μl of TMB Substrate Solution (tetramethylbenzidine) were added to each well. Microwell strips were incubated at room temperature (18° to 25° C.) for 30 min., and direct exposure to intense light was avoided.

The enzyme reaction was stopped by quickly pipetting 100 μl of Stop Solution (1M Phosphoric acid) into each well. The absorbance of each microwell was read on a spectrophotometer using 450 nm as the primary wave length (optionally 620 nm as the reference wave length; 610 nm to 650 nm is acceptable). The plate reader was blanked according to the manufacturer's instructions by using the blank wells. The absorbance of both the samples and the standards was determined. The average absorbance values for each set of duplicate standards and samples were calculated.

A standard curve was created by plotting the mean absorbance for each standard concentration on the ordinate against the human galectin-3 concentration on the abscissa. A best fit curve was drawn through the points of the graph. See FIG. 2.

The concentration of circulating human galectin-3 may be determined for each sample, by finding the mean absorbance value on the ordinate and extending a horizontal line to the standard curve. At the point of intersection, a vertical line was extended to the abscissa and the corresponding human galectin-3 concentration was read.

Figure 2:
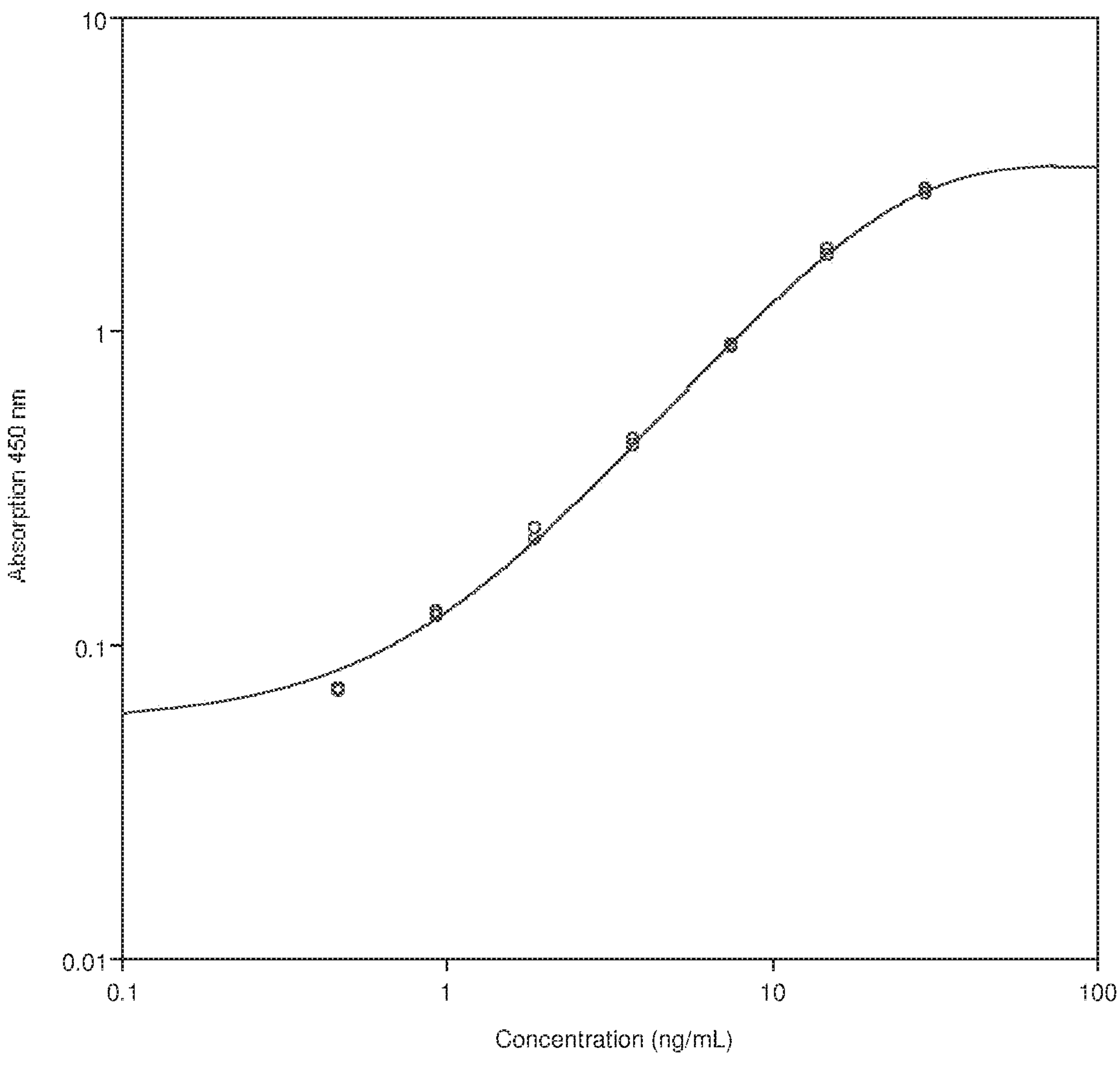
FIG. 2 is an exemplary hypothetical standard curve relating signal to galectin-3 concentration useful in explaining the nature of the invention.

Because the samples were diluted 1:5 (20 μl sample+80 μl Sample Diluent), the concentration read from the standard curve was multiplied by the dilution factor (×5). A representative standard curve is shown in FIG. 2.

TABLE 2

Typical data using the human galectin-3 ELISA
Measuring wavelength: 450 nm
Reference wavelength: 620 nm

| Standard | Human Galectin-3 Concentration (ng/ml) | O.D. at 450 nm | Mean O.D. at 450 nm | C.V. (%) |
|---|---|---|---|---|
| 1 | 30.00 | 2.824 | 2.778 | 2.3 |
| | 30.00 | 2.733 | | |
| 2 | 15.00 | 1.812 | 1.767 | 3.5 |
| | 15.00 | 1.723 | | |
| 3 | 7.50 | 0.889 | 0.890 | 0.2 |
| | 7.50 | 0.892 | | |
| 4 | 3.75 | 0.431 | 0.440 | 2.9 |
| | 3.75 | 0.449 | | |
| 5 | 1.88 | 0.232 | 0.223 | 5.7 |
| | 1.88 | 0.214 | | |
| 6 | 0.94 | 0.123 | 0.124 | 1.6 |
| | 0.94 | 0.126 | | |
| 7 | 0.47 | 0.071 | 0.072 | 1.8 |
| | 0.47 | 0.072 | | |
| Blank | 0 | 0.018 | 0.018 | |
| | 0 | 0.018 | | |

Performance Characteristics

Sensitivity

The limit of detection (LoD) of human galectin-3 defined as the analyte concentration resulting in an absorbance significantly higher than that of the dilution medium (mean plus 3 standard deviations) was determined to be 0.09 ng/ml (mean of 12 independent assays).

Reproducibility

Intra-assay reproducibility (reproducibility within the assay) was evaluated in 4 independent experiments. Each assay was carried out with 6 replicates of 8 plasma samples containing different concentrations of human galectin-3. Two standard curves were run on each plate. Data below show the mean human galectin-3 concentration and the coefficient of variation for each sample (see Table 3). The calculated overall intra-assay coefficient of variation was 4.2%.

TABLE 3

The mean human galectin-3 concentration and the coefficient of variation for each sample

| Sample | Experiment | Mean Human Galectin-3 Concentration (ng/ml) | Coefficient of Variation (%) |
|---|---|---|---|
| 1 | 1 | 70.5 | 2.9 |
| | 2 | 66.2 | 5.5 |
| | 3 | 71.6 | 3.8 |
| | 4 | 71.8 | 3.1 |
| 2 | 1 | 38.9 | 4.4 |
| | 2 | 42.7 | 2.0 |
| | 3 | 39.4 | 2.0 |
| | 4 | 38.9 | 3.7 |
| 3 | 1 | 4.9 | 4.6 |
| | 2 | 4.9 | 7.6 |
| | 3 | 4.9 | 3.2 |
| | 4 | 4.4 | 3.0 |

TABLE 3-continued

The mean human galectin-3 concentration and the coefficient of variation for each sample

| Sample | Experiment | Mean Human Galectin-3 Concentration (ng/ml) | Coefficient of Variation (%) |
|---|---|---|---|
| 4 | 1 | 8.6 | 5.9 |
| | 2 | 9.1 | 3.5 |
| | 3 | 8.7 | 5.5 |
| | 4 | 8.2 | 7.7 |
| 5 | 1 | 20.8 | 4.5 |
| | 2 | 21.6 | 3.4 |
| | 3 | 21.3 | 4.6 |
| | 4 | 22.5 | 2.7 |
| 6 | 1 | 90.9 | 3.0 |
| | 2 | 90.9 | 6.4 |
| | 3 | 85.5 | 4.5 |
| | 4 | 84.2 | 5.8 |
| 7 | 1 | 57.2 | 2.2 |
| | 2 | 58.0 | 3.0 |
| | 3 | 57.1 | 2.4 |
| | 4 | 54.8 | 4.7 |
| 8 | 1 | 42.6 | 5.7 |
| | 2 | 44.4 | 4.0 |
| | 3 | 42.2 | 2.8 |
| | 4 | 46.6 | 5.8 |

Inter-assay reproducibility (assay to assay reproducibility within one laboratory) was evaluated in 4 independent experiments. Each assay was carried out with 6 replicates of 8 plasma samples containing different concentrations of human galectin-3. Two standard curves were run on each plate. Data below show the mean human galectin-3 concentration and the coefficient of variation calculated on 24 determinations of each sample. The calculated overall inter-assay coefficient of variation was 4.0%.

TABLE 4

The mean human galectin-3 concentration and the coefficient of variation of each sample

| Sample | Mean Human Galectin-3 Concentration (ng/ml) | Coefficient of Variation (%) |
|---|---|---|
| 1 | 70.0 | 3.7 |
| 2 | 40.0 | 4.6 |
| 3 | 4.8 | 5.0 |
| 4 | 8.7 | 4.2 |
| 5 | 21.5 | 3.3 |
| 6 | 87.9 | 4.0 |
| 7 | 56.8 | 2.4 |
| 8 | 44.0 | 4.6 |

Spike Recovery

The spike recovery was evaluated by spiking 3 levels of human galectin-3 into 3 individual plasma samples. Recoveries were determined in 4 independent experiments with 2 replicates each. The unspiked plasma samples were used as blank in these experiments. The overall mean recovery was 101% (see Table 5).

TABLE 5

| | | spike recovery in % | | | |
|---|---|---|---|---|---|
| sample | concentration | plate 1 | plate 2 | plate 3 | plate 4 |
| Spike 1 in #1 | 70 ng/ml | 100% | 116% | 108% | 106% |
| Spike 2 in #1 | 40 ng/ml | 102% | 109% | 86% | 106% |
| Spike 3 in #1 | 8 ng/ml | 97% | 108% | 96% | 103% |
| Spike 1 in #2 | 70 ng/ml | 93% | 92% | 97% | 107% |
| Spike 2 in #2 | 40 ng/ml | 104% | 113% | 98% | 110% |
| Spike 3 in #2 | 8 ng/ml | 112% | 96% | 110% | 89% |
| Spike 1 in #3 | 70 ng/ml | 99% | 97% | 98% | 100% |
| Spike 2 in #3 | 40 ng/ml | 96% | 108% | 105% | 104% |
| Spike 3 in #3 | 8 ng/ml | 112% | 82% | 93% | 93% |

Dilution Parallelism

Four plasma samples with different levels of human galectin-3 were analyzed at serial 2 fold dilutions. Recoveries were determined in 4 independent experiments with 4 replicates each. The overall mean recovery was 88.6% (see Table 6).

TABLE 6

| Sample | Dilution | Expected Human Galectin-3 Concentration (ng/ml) | Observed Human Galectin-3 Concentration (ng/ml) | Recovery of Expected Human Galectin-3 Concentration (%) |
|---|---|---|---|---|
| 1 | 1:5 | — | 23.9 | — |
| | 1:10 | 11.9 | 11.2 | 94.1 |
| | 1:20 | 6.0 | 5.4 | 90.4 |
| | 1:40 | 3.0 | <S7 | — |
| 2 | 1:5 | — | 62.8 | — |
| | 1:10 | 31.4 | 27.9 | 88.9 |
| | 1:20 | 15.7 | 13.7 | 87.4 |
| | 1:40 | 7.8 | 7.0 | 89.5 |
| 3 | 1:5 | — | 81.5 | — |
| | 1:10 | 40.7 | 36.9 | 90.5 |
| | 1:20 | 20.4 | 18.3 | 90.0 |
| | 1:40 | 10.2 | 8.2 | 80.6 |
| 4 | 1:5 | — | 40.4 | — |
| | 1:10 | 20.2 | 18.8 | 93.1 |
| | 1:20 | 10.1 | 8.7 | 86.2 |
| | 1:40 | 5.1 | 4.3 | 86.0 |

Sample Stability

Freeze-Thaw Stability

Aliquots of plasma samples were stored at −20° C. and thawed 3 times, and the human galectin-3 levels determined. There was no significant loss of human galectin-3 immunoreactivity detected by freezing and thawing.

Storage Stability

Aliquots of plasma samples were stored at −20° C., 2-8° C., room temperature (RT) and at 37° C., and the human galectin-3 level determined after 24 h. There was no significant loss of human galectin-3 immunoreactivity detected during storage under the above conditions.

Example 2A: A Kit for Detecting Galectin-3

Table 7 shows the components of an exemplary kit for the detection of galectin-3.

TABLE 7

| Galectin-3 assay reagents | | | |
|---|---|---|---|
| Qty | Name | Description | Abbreviation |
| 1 plate | Plate | Ready-to-use microtiter plate coated with anti-galectin-3 monoclonal antibody (M3/38) | (P) |
| 1 bottle | Assay Diluent* | Phosphate buffered saline with 1% bovine serum albumin (45 mL) | (AD) |
| 1 bottle | TMB substrate | Tetramethyl benzidine (15 mL) | (TS) |
| 1 bottle | Stop solution | 0.5M sulfuric acid (10 mL) | (ST) |
| 2 bottles | Wash buffer concentrate* | 0.5M Tris buffered saline (2 × 50 mL; 10X concentrate) | (WC) |
| 1 bottle | Detection concentrate* | Horseradish peroxidase (HRP) labeled mouse anti-human galectin-3 antibody 87B5 (0.4 mL) | (DC) |
| 2 vials | Standard | Recombinant human galectin-3, 12 ng per vial (lyophilized) | (S1) |
| 2 vials | Low Quality Control (QC)† | Low QC material, Recombinant human galectin-3 in protein matrix (lyophilized) | (C1) |
| 2 vials | High Quality Control (QC)† | High QC material, Recombinant human galectin-3 in protein matrix (lyophilized) | (C2) |
| 2 | Plate seals | Adhesive plastic plate seals | |

*Contains ProClin ® preservative.

†Contains processed human plasma tested negative or nonreactive for anti-HIV-1/2, anti-HCV and HBsAg when tested by an FDA approved method.

One anti-galectin-3 antibody, M3/38, was coated onto the surface of the wells in a microtiter plate and served as the capture antibody to bind galectin-3 molecules in samples, while the other anti-galectin-3 antibody, a horseradish peroxidase (HRP)-labeled anti-galectin-3 antibody (87B5) was provided in solution and functions as the detection antibody for detecting galectin-3 molecules bound to the capture antibody. While M3/38 and 87B5 were used in this example, use of these specific antibodies is not required with the kits and methods of the present invention.

Galectin-3 controls (C1 and C2) were comprised of a protein matrix spiked with recombinant human galectin-3.

Example 2B: Detection of Recombinant Galectin-3 Controls

The kit of Example 2A was used in a microtiter plate-based ELISA assay to quantitate galectin-3 levels. Included in the kit were two monoclonal antibodies against galectin-3. In the assay, described in greater detail in the following paragraph, standards and quality control materials were introduced into the wells and incubated for 60 minutes. During this incubation, the galectin-3 present in the standards was bound to the capture antibody coated onto the well surface. A subsequent wash step removed all unbound material introduced with the sample including unbound galectin-3. The detection antibody was then introduced into the well and incubated for 60 minutes. During this time, an antibody-antigen-antibody complex was formed. After a wash step to remove any unbound detection antibody, the Tetramethyl benzidine (TMB) substrate was added, yielding a blue color in the presence of HRP. The color development was stopped after 20 minutes by the addition of sulfuric acid, changing the color to yellow that was read at an absorbance of 450 nm. The test results of the specimens were read from the calibration curve. The absorbance was proportional to the galectin-3 levels in the specimens.

Prior to use, all assay components were brought room temperature for 30 minutes. After opening the pouch containing the plates, the top surface of each strip was numbered with permanent ink in case they were unintentionally released from the plate frame. Using deionized water, a 1:10 dilution of 10× wash concentrate (WC) was prepared. Diluted buffer was stored at 2-8° C.

The set of seven galectin-3 standards was prepared by serial dilution of the standard (S1, recombinant human galectin-3, 12 ng per vial). The calibration range was 0.156 ng/mL to 10.0 ng/mL.

Before use, one vial of the galectin-3 standard (S1) was reconstituted with 300 μL of deionized water followed by addition of 900 μL of Assay Diluent. The vial was allowed to stand 15-20 minutes at room temperature with periodic vortexing and gentle inversion ensuring that the reconstitution water wets the entire surface area inside the vial. Complete dissolution of the standard was obtained prior to use.

One vial of each of the galectin-3 controls (C1 and C2) was reconstituted with 250 μL deionized water. Vials were allowed to stand 15-20 minutes at room temperature with periodic vortexing and gentle inversion ensuring that the reconstitution water wets the entire surface area inside the vial. Complete dissolution of C1 and C2 was obtained prior to use.

Each reconstituted control (C1 and C2) was diluted 10-fold (1:10) using the Assay Diluent (AD) in a disposable borosilicate glass or polypropylene or other low protein-binding plastic test tube or vial. Each dilution was mixed by vortexing or inversion. A minimum of 25 μL of the reconstituted control was used for the dilution. Dilutions were performed externally (i.e. no in-well dilutions) and immediately before use.

Standards were diluted immediately before use. Six disposable tubes were labeled with numbers 2 to 7. 250 μL assay diluent (AD) were pipetted into each labeled tube. Next, 250 μL galectin-3 standard (S1) were pipetted to tube 2 and mixed gently. Then, 250 μL were transferred from tube 2 to tube 3 and vortexed gently. Next, 250 μL were transferred from tube 3 to 4, and the process was continued through tube 7.

Microtiter plate wells were designated for each of the controls, diluted standards and blank. All samples were tested in duplicate (i.e. blank, diluted standards, and controls).

100 μl of each sample were transferred directly from the dilution vessels into duplicate wells of the microtiter plate covered with galectin-3 capture antibody. The wells were covered with a clean plate seal and incubated for 1 hour at 20-25° C. without shaking.

While the plate was incubating, the labeling antibody was diluted 1:30 with the Assay Diluent according to the dilution scheme shown in Table 8 below:

TABLE 8

Recommended Dilution Scheme for Detection Concentrate (30x)*

| No of Strips | AD μL | DC μL |
|---|---|---|
| 1 | 1537 | 53 |
| 2 | 2320 | 80 |
| 3 | 3103 | 107 |
| 4 | 3886 | 134 |
| 5 | 4669 | 161 |
| 6 | 5452 | 188 |
| 7 | 6235 | 215 |
| 8 | 7018 | 242 |
| 9 | 7801 | 269 |
| 10 | 8584 | 296 |
| 11 | 9367 | 323 |
| 12 | 10150 | 350 |

*AD = Assay Diluent; DC = Detection Concentrate.

Next, the plate seal was removed and the wells were washed with 400 μL diluted wash buffer per well, using a mechanical washer programmed to run 4 wash cycles, with 15 seconds soak time per cycle. After the fourth wash, wells were emptied by tapping them on an absorbent paper towel.

Next, 100 μL of diluted detection solution were pipetted to each well. Wells were covered with a clean plate seal and incubated 1 hour at 20-25° C. without shaking. The plate seal was removed and the wells were washed with 400 μL diluted wash buffer per well, using a mechanical washer programmed to run 4 wash cycles, with 15 seconds soak time per cycle. After the fourth wash, wells were emptied by tapping them on an absorbent paper towel.

100 μL of TMB-substrate (TS) were pipetted to each well and the plate incubated for 20 minutes at 20-25° C. in the dark.

50 μL of stop solution (ST) were pipetted to each well. The contents of each well were mixed by drawing the contents up and down using a clean pipette tip, or by gently tapping the side of the plate. The contents of the well turned from blue to yellow. Any bubbles were removed from the liquid surface of each well, and any dirt or liquid was removed from the well exterior.

The absorbance of each well was measured in a microtiter plate reader at 450 nm within 30 minutes of the stop solution addition.

After completing the assay steps, the absorbance of each standard and control was read at 450 nm using the microplate reader. A standard curve for the assay was determined using the following procedure. The average absorbance of the blank was subtracted from all data, including standards and controls. The average, standard deviation, and coefficient of variation (CV) of the absorbance ($Abs_{450}$) value were calculated for each set of duplicate standards and controls. If either of the controls had a duplicate CV greater than 20%, the entire plate was rejected and all specimens were re-analyzed using new reagents. Appropriate curve-fitting tools for third order polynomial curve fitting with least squares optimization of the means were used from each standard dilution. The measured concentration was multiplied by 10 (dilution factor of specimens and controls) to obtain the final galectin-3 concentration. Control values were verified to be within acceptable ranges. The blank value was verified to be lower than the lowest calibrator. If the blank value exceeded the lowest calibrator value (e.g. the low calibrator value is negative when the blank is subtracted), the assay was repeated.

Figure 3:
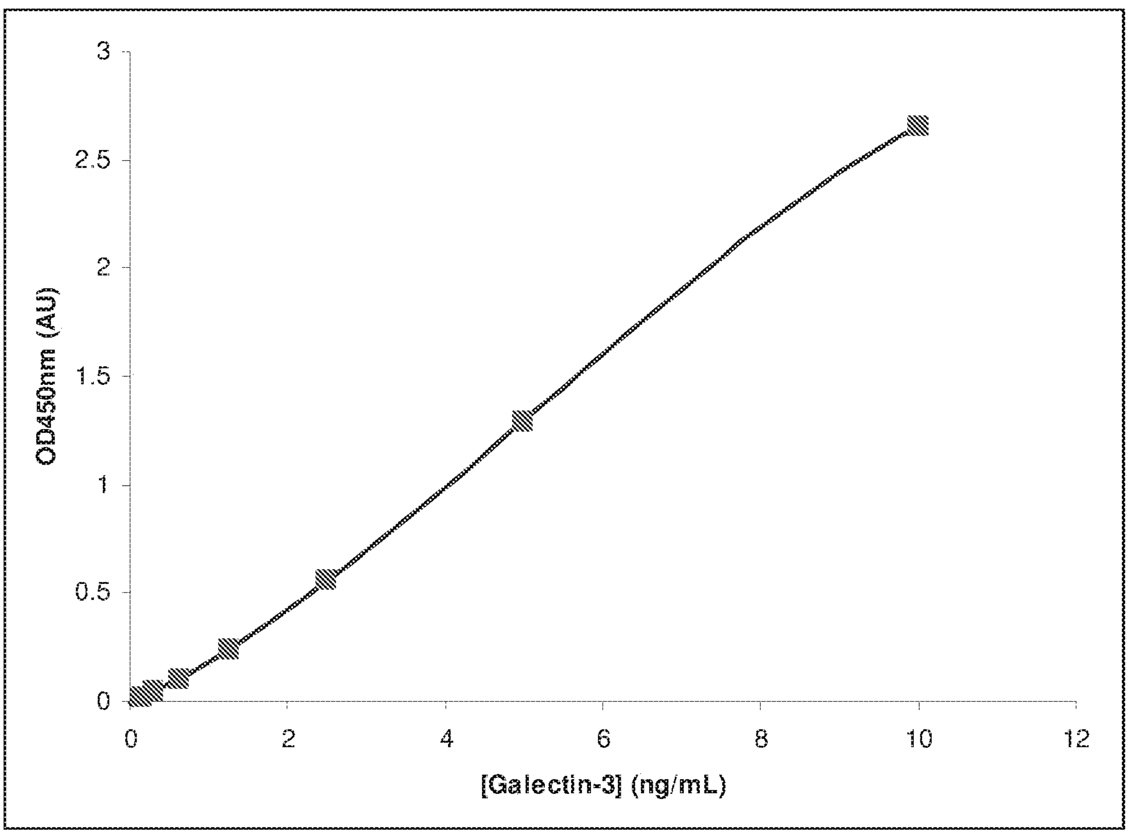
FIG. 3 is an exemplary second hypothetical standard curve relating signal to galectin-3 concentration useful in explaining the nature of the invention.

A representative calibration curve is shown in FIG. 3 and representative values for the absorbance of each diluted standard are shown in Table 9.

TABLE 9

A Representative Calibration Curve and Typical Absorbance Values at 450 nm

| Dilution | Galectin-3 Concentration (ng/mL) | $Abs_{450\ nm}$ |
|---|---|---|
| 1 | 10.0 | 2.690 |
| 2 | 5.0 | 1.326 |
| 3 | 2.5 | 0.595 |
| 4 | 1.25 | 0.269 |
| 5 | 0.625 | 0.131 |
| 6 | 0.313 | 0.082 |
| 7 | 0.156 | 0.054 |
| Blank | 0 | 0.033 |

Example 2C: Detection of Recombinant Galectin-3 in Clinical Samples

The methods outlined in Example 2B were performed with the addition of clinical samples, incorporating the additional steps outlined below.

While Standard and Controls were reconstituting, each test specimen was diluted 10-fold (1:10) using the Assay Diluent (AD) in a disposable borosilicate glass or polypropylene or other low protein-binding plastic test tube or vial. Each dilution was mixed by vortexing or inversion, with a minimum of 25 μL of serum or plasma being used for the dilution. Dilutions were performed externally (i.e. no in-well dilutions) and immediately before use.

After completing the assay steps, the absorbance of each specimen was read at 450 nm using the microplate reader. The absorbance was proportional to the concentration of galectin-3 in the specimens. Galectin-3 concentrations in the specimens and controls were based on the relationship of the absorbance of the specimens compared to that of the standards, which have a known concentration of galectin-3.

The standard curve for the assay was assigned for each individual plate using the following procedure. The average absorbance of the blank was subtracted from all data, including standards, controls and test specimens. The average, standard deviation, and coefficient of variation (CV) of the absorbance ($Abs_{450}$) value were calculated for each set of duplicate standards, controls and test specimens. Specimens with duplicate CVs greater than 20% were re-analyzed. If either of the controls had a duplicate CV greater than 20%, the entire plate was rejected and all specimens were re-analyzed using new reagents. Appropriate curve-fitting tools for third order polynomial curve fitting with least squares optimization of the means were used from each standard dilution. Concentrations of unknown specimens and controls were calculated based upon the third order polynomial equation. The measured concentration was multiplied by 10 (dilution factor of specimens and controls) to obtain the final galectin-3 concentration. Control values were verified to be within acceptable ranges. When an unacceptable result from assay controls was obtained, the assay was repeated. The blank value was verified to be lower than the lowest calibrator. If the blank value exceeded the lowest calibrator value (e.g. the low calibrator value is negative when the blank is subtracted), the assay was repeated.

Measuring Range of the Assay

The measuring range of the galectin-3 assay with clinical specimens was demonstrated to be from 1.32 to 96.6 ng/mL. The assay was calibrated with seven standards spanning the range of approximately 0.1 to 10.0 ng/mL. Each test sample (i.e. control or subject specimen) was pre-diluted 1:10 prior to assay allowing the measurement to occur within the range bracketed by the calibrators. The linearity of the assay was established according to the recommendations of the Clinical Laboratory Standards Institute Evaluation Protocol 6 (CLSI-EP6). Serum and plasma specimens were prepared and diluted to span a clinically-meaningful measurement range of galectin-3 concentrations. The assay was demonstrated to be linear up to 96.6 ng/mL. The lower end of the measuring range is defined by the limit of quantitation (LoQ), which was determined to be 1.32 ng/mL.

Performance Characteristics

Precision

Precision of the galectin-3 assay was assessed in an evaluation according to the CLSI EP5-A2 Guidelines. Three plasma pools spanning a range of galectin-3 concentrations were analyzed in duplicate with two runs per day over twenty days. Estimates of within-run, run-to-run, day-to-day and total precision were calculated and deemed to be acceptable. Results are summarized in Table 10.

TABLE 10

Precision of the Galectin-3 assay

| Test Specimen | Galectin-3 mean (ng/mL) | Within run SD | Within run CV % | Run to run SD | Run to run CV % | Day to day SD | Day to day CV % | Total SD | Total CV % |
|---|---|---|---|---|---|---|---|---|---|
| Low | 6.1 | 0.3 | 5.7 | 0.6 | 10.5 | 0.0 | 0.0 | 0.7 | 12.0 |
| Mid | 20.7 | 0.7 | 3.4 | 1.4 | 6.7 | 0.3 | 1.7 | 1.6 | 7.7 |
| High | 72.2 | 2.4 | 3.3 | 4.3 | 6.0 | 2.9 | 4.0 | 5.7 | 8.0 |

Precision was also evaluated at three CLIA-certified clinical laboratories according the CLSI EP5-A2 guidelines. Total coefficients of variation (CVs) ranged from 5.60% to 16.89% across the three CLIA-certified clinical laboratory sites with all sites providing acceptable results.

Analytical Sensitivity

The analytical sensitivity of the galectin-3 assay was established according to the recommendation of the CLSI EP17-A Guidelines.

Limit of Blank (LoB): LoB=0.86 ng/mL

Limit of Detection (LoD): LoD=1.13 ng/mL

Limit of Quantitation (LoQ): LoQ=1.32 ng/mL

Analytical Specificity

The galectin-3 assay displayed no significant cross-reactivity when tested in the presence of the following compounds: galectin-1, galectin-2, galectin-4, galectin-7, galectin-8, galectin-9, galectin-12, collagen I and collagen III, all at a concentration of 500 ng/mL. The mean % cross-reactivity of the above potential cross-reactants is at or below 0.3%.

Linearity

Linearity over the measuring range was assessed according to the recommendations of the CLSI-EP6. Samples were prepared by spiking galectin-3 into serum and plasma specimens followed by analysis with the galectin-3 assay. Results show the assay is linear from 1.24 to 96.6 ng/mL. The lower end of the measuring range is defined by the limit of quantitation (LoQ), which was determined to be 1.32 ng/mL in a separate study.

In summary, the measuring range of the galectin-3 assay is from 1.32 ng/ml to 96.6 ng/mL.

Interfering Substances

The galectin-3 assay was evaluated for the effects of potential interfering substances, both endogenous and exogenous, according to the recommendations of the CLSI EP7-A. Conjugated bilirubin (up to 5 mg/dL), unconjugated bilirubin (up to 15 mg/dL), albumin (BSA, up to 12 g/dL), triglycerides (up to 3000 mg/dL), cholesterol (up to 250 mg/dL) and creatinine (up to 5 mg/dL) do not show any interference in the assay. Purified hemoglobin (up to 500 mg/dL) did not show interference in the galectin-3 assay; however, packed blood cell lysate does show interference. Human anti-mouse antibodies (HAMA) and rheumatoid factor (RF) cause significant positive interference with the galectin-3 assay.

The galectin-3 assay was not significantly affected when tested in the presence of 34 common pharmaceutical substances; including HF drugs (refer to Table 11).

TABLE 11

| Common Drugs That Did Not Show Interference with the Galectin-3 assay |
|---|
| Acetaminophen |
| Acetylsalicylic acid |
| Amlodipine |
| Ampicillin |
| Ascorbic Acid |
| Atenolol |
| Caffeine |
| Carvedilol |
| Captopril |
| Chloramphenicol |
| Diclofenac |
| Digoxin |
| Diltiazem |
| Disopyramide |
| Dopamine |
| Enalaprilat |
| Furosemide |
| Hydrochlorothiazide |
| Ibuprofen |
| Indomethacin |
| Lidocaine |
| Lisinopril |
| Losartan |
| Lovastatin |
| Methyldopa |
| Metoprolol |
| Naproxen |
| Nifedipine |
| Quinidine |
| Ramipril |
| Spironolactone |
| Theophylline |
| Verapamil |
| Warfarin |

High Dose Hook Effect

There is no high dose hook effect at galectin-3 levels up to 500 ng/mL.

Spike Recovery

In a study where human galectin-3 was spiked into 6 subject matched serum and EDTA-plasma samples as well as Assay Diluent at 5 different spiking levels: 15 ng/mL; 25 ng/mL, 50 ng/mL, 75 ng/mL and 90 ng/mL, the mean percent recovery in serum ranged from 79.7% to 84.6% with grand mean percent recovery of 81.7% and the mean percent recovery in EDTA-plasma ranged from 71.4% to 81.4% with grand mean percent recovery of 78.1%. This study demonstrated a difference in recovery of spiked amounts of galectin-3 in serum/plasma matrices compared to the Assay Diluent matrix. Although this effect will likely be observed in similar spike recovery experiments, it does not have an impact on clinical measurements.

Example 2D: Detection of Galectin-3 in Clinical Samples from Subjects without Known Heart Disease In a prospective, observational study, galectin-3 levels were determined by analysis of 1,092 banked plasma samples from subjects without known heart disease but that otherwise resemble, by age and gender distribution, the HF patient population. Specimens were from women between the ages of 60 and 80 years (n=572) and men between the ages of 55 and 80 (n=520). This reference population comprised individuals of different ethnic background, as follows: Black (n=305, 27.9%), Caucasian (n=686, 62.8%), Hispanic (n=42, 3.8%), Asian or Pacific Islander (n=30, 2.7%), and not specified (n=29, 2.7%). Blood plasma samples were collected from study participant into tubes containing EDTA. The blood was processed and blood plasma was subsequently frozen at −20° C. or colder.

All subjects had detectable galectin-3 levels using the galectin-3 assay described in Example 2C. A non-parametric method using the distribution of galectin-3 reference range values (refer to Table 12) established a single threshold of 17.6 ng/mL for galectin-3 based upon an upper limit of normal (ULN) value. ULN is defined as the 90$^{th}$ percentile of the distribution of galectin-3 values, independent of gender or age.

TABLE 12

Distribution of Galectin-3 Levels

| | Galectin-3 Concentration (ng/mL) | | | | |
|---|---|---|---|---|---|
| Percentile | All Subjects (n = 1092) | Males (n = 520) | Females (n = 572) | Age >65 yrs (n = 720) | Age ≤65 yrs (n = 372) |
| 5$^{th}$ | 6.2 | 5.8 | 6.4 | 6.3 | 5.9 |
| 25$^{th}$ | 9.5 | 8.8 | 10.5 | 9.9 | 9.0 |
| 50$^{th}$ | 12.0 | 11.1 | 12.7 | 12.4 | 11.1 |
| 75$^{th}$ | 14.7 | 13.8 | 15.5 | 15.1 | 14.1 |
| 90$^{th}$ | 17.6 | 16.3 | 18.7 | 18.0 | 16.6 |
| 95$^{th}$ | 20.3 | 18.3 | 21.1 | 20.5 | 19.2 |

Figure 4:
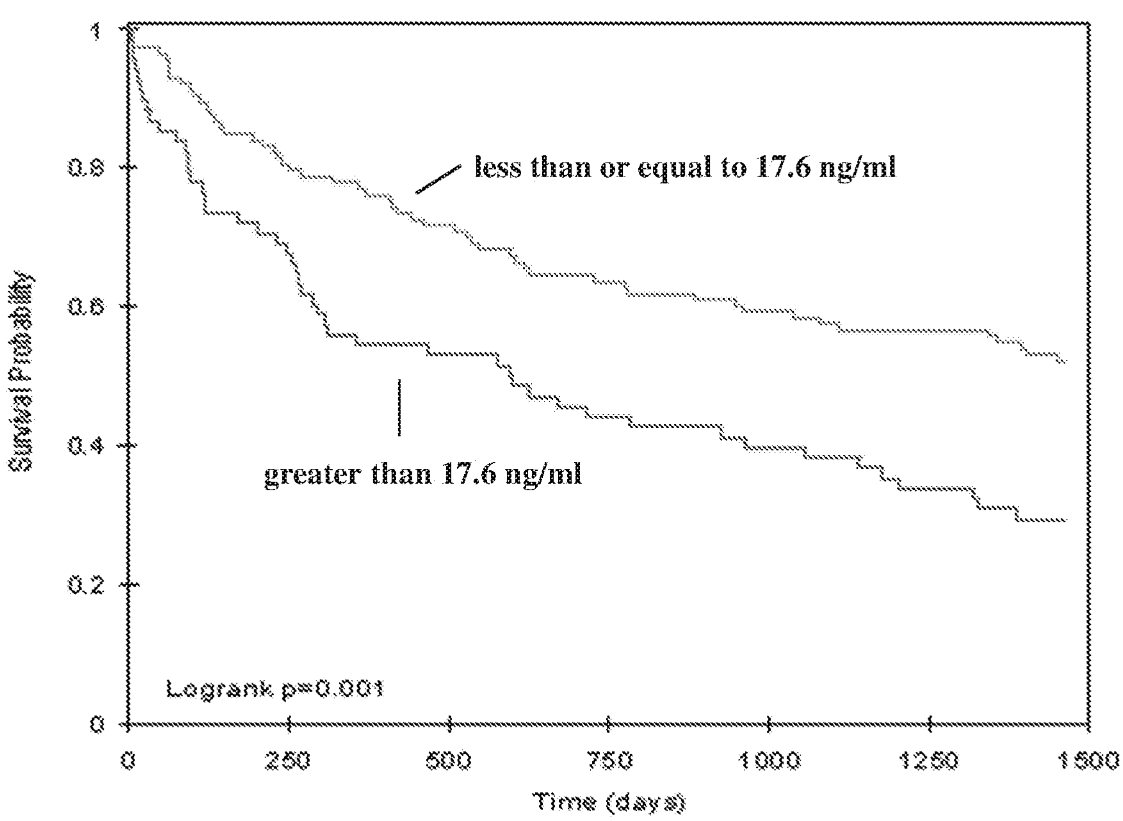
FIG. 4 is an exemplary survival probability curve for subjects with baseline galectin-3 level above and below a threshold value of 17.6 ng/ml in the acute decompensated HF study described in Example 2E.

Example 2E: Detection of Galectin-3 in Clinical Samples from Subjects with Acute Decompensated HF To assess the utility of the galectin-3 assay described in Example 2C in subjects diagnosed with acute decompensated HF, galectin-3 levels were measured in 181 banked EDTA-plasma samples from the Acute Decompensated Heart Failure (ADHF) study. The ADHF study was a prospective observational study conducted in the United States that enrolled subjects who presented with dyspnea in the emergency department (4). Blood plasma galectin-3 concentration was measured in baseline samples for 181 subjects diagnosed with acute decompensated HF. Subjects were followed-up for four years. The galectin-3 threshold value of 17.6 ng/mL, derived from the reference range population (described in Example 2D), was used to define a category of subjects with elevated baseline galectin-3 (n=68). Patients had a hazard of death approximately 3-fold higher in the highest quartile of galectin-3 levels compared to the lowest quartile. Cox regression survival analysis and Kaplan-Meier analysis demonstrated that elevated baseline galectin-3 is a significant predictor of risk of mortality, even after adjustment for age, gender, New York Heart Association (NYHA) class, left ventricular ejection fraction, smoking status, and diabetes status (see FIG. 4).

TABLE 13

Hazard Ratios of Mortality for HF Subjects in ADHF Study

| | Galectin-3 Hazard Ratio (95% CI, p value) | |
|---|---|---|
| | less than or equal to 17.6 ng/mL | greater than 17.6 ng/mL |
| Number of subjects | 113 | 68 |
| Model 1 (univariate) | 1.0 | 1.90 (1.29-2.80, p = 0.001) |
| Model 2 (adjusted for age and gender) | 1.0 | 1.59 (1.02-2.37, p = 0.022) |
| Number of deaths at 48 months | 54/113 (47.8%) | 48/68 (70.6%) |

Example 2F: Detection of Galectin-3 in Clinical Samples from Subjects Chronic Heart Failure (Chronic HF Study I)

Figure 5:
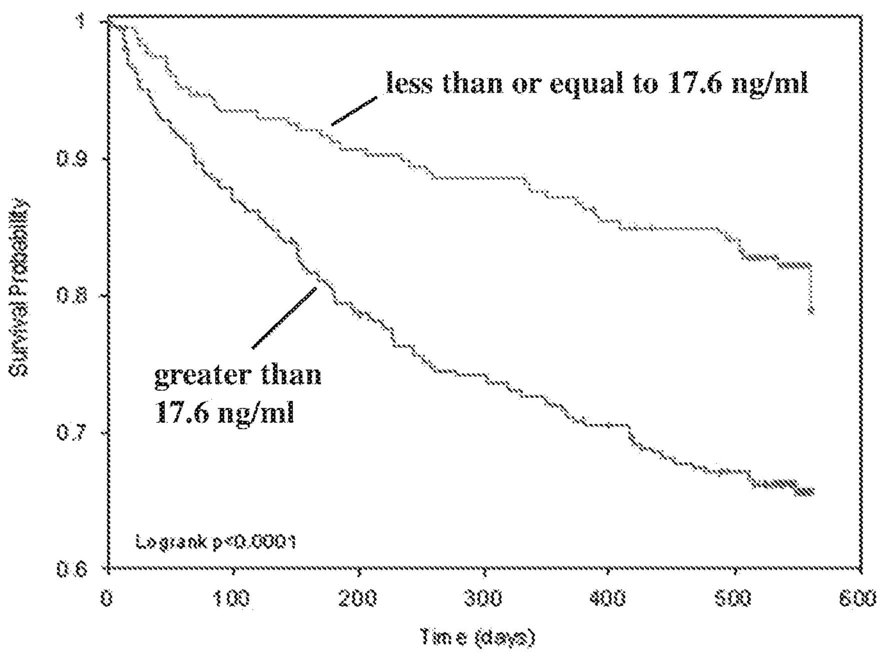
FIG. 5 is an exemplary survival probability curve for subjects with baseline galectin-3 level above and below a threshold value of 17.6 ng/ml in the Chronic HF Study I described in Example 2F.

The Chronic HF Study I involved NYHA class II to IV diagnosed on the basis of a combination of typical signs and symptoms for which hospitalization was considered necessary, including the need for intravenously administered medication. Subjects were enrolled upon discharge from the hospital at which time they had to be stable with standard medication. Galectin-3 concentration was measured by using the galectin assay on the available baseline samples for 592 subjects. The galectin-3 threshold value of 17.6 ng/mL, derived from the reference range population (described in Example 2D), was used to define a category of subjects with elevated baseline galectin-3 (n=363). The hazard of death at any time after discharge from the hospital was approximately 3-fold higher for patients in the highest quartile of galectin-3 levels compared to the lowest quartile. Cox regression survival analysis and Kaplan-Meier analysis demonstrated that elevated baseline galectin-3 is a significant predictor of risk of mortality, even after adjustment for age, gender, New York Heart Association (NYHA) class, left ventricular ejection fraction, smoking status, and diabetes status (see FIG. 5).

TABLE 14

Hazard Ratios of Mortality for HF Subjects in Chronic HF Study I

| | Galectin-3 Hazard Ratio (95% CI, p value) | |
|---|---|---|
| | less than or equal to 17.6 ng/mL | greater than 17.6 ng/mL |
| Number of subjects | 229 | 363 |
| Model 1 (univariate) | 1.0 | 2.07 (1.45-2.93, p < 0.001) |
| Model 2 (adjusted for age and gender) | 1.0 | 1.95 (1.36-2.79, p < 0.001) |

TABLE 14-continued

Hazard Ratios of Mortality for HF Subjects in Chronic HF Study I

| | Galectin-3 Hazard Ratio (95% CI, p value) | |
|---|---|---|
| | less than or equal to 17.6 ng/mL | greater than 17.6 ng/mL |
| Number of deaths at 15 months (for subjects with follow-up ≥15 months) | 34/222 (15.3%) | 116/353 (32.9%) |

Example 2G: Detection of Galectin-3 in Clinical Samples from Subjects Chronic Heart Failure (Chronic HF Study II)

The Chronic HF Study II enrolled patients with chronic NYHA class III or IV HF. A diagnosis of HF was established by typical clinical signs and symptoms of HF in conjunction with echocardiographic or radionuclide ventriculographic findings of a reduced left ventricular systolic function or left ventricular ejection fraction (LVEF), or of a diastolic dysfunction with preserved left ventricular systolic function. Patients were stable with standard medication at the time of enrollment.

Figure 6:
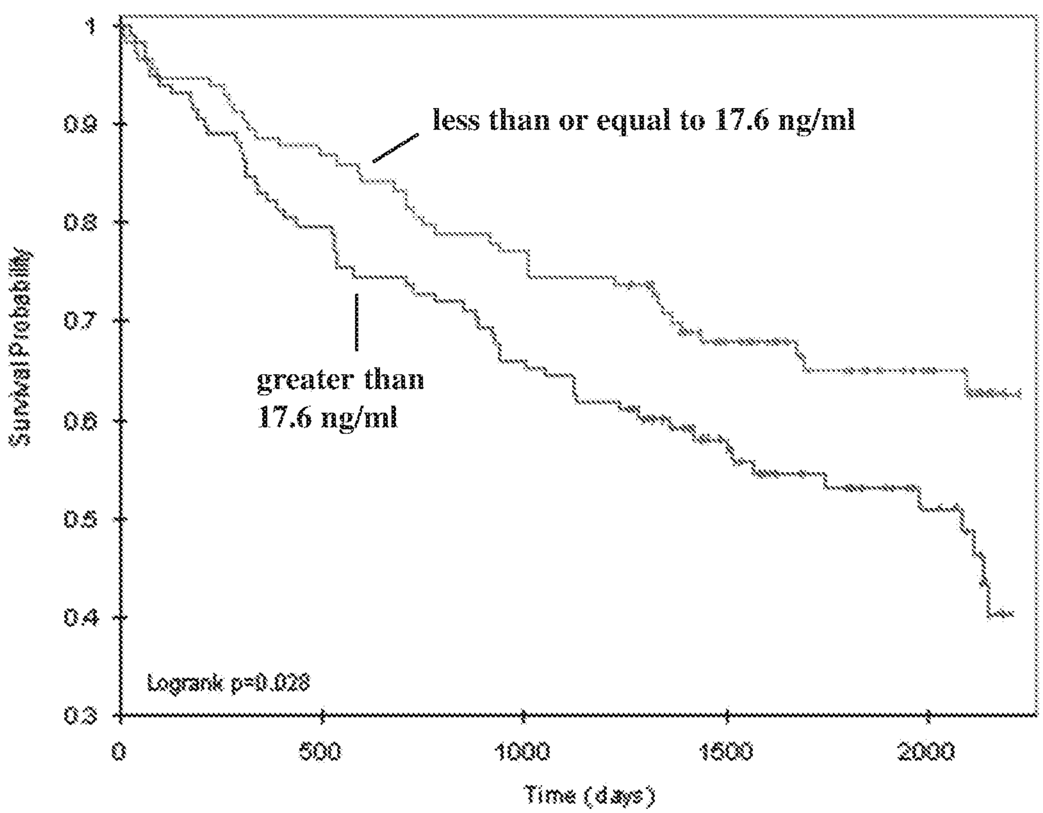
FIG. 6 is an exemplary survival probability curve for subjects with baseline galectin-3 level above and below a threshold value of 17.6 ng/ml in the Chronic HF Study II described in Example 2G.

Galectin-3 concentration was measured using the galectin assay on baseline samples for 232 subjects. The galectin-3 threshold value of 17.6 ng/mL, derived from the reference range population (described in Example 2D), was used to define a category of subjects with elevated baseline galectin-3 (n=118). patients in the highest quartile of galectin-3 levels compared to the lowest quartile showed an approximately 2-fold higher hazard of death over a 3-6 year follow-up period. Cox regression survival analysis and Kaplan-Meier analysis demonstrated that elevated baseline galectin-3 is a significant predictor of risk of mortality, even after adjustment for age, gender, New York Heart Association (NYHA) class, left ventricular ejection fraction, smoking status, and diabetes status (see FIG. 6).

TABLE 15

Hazard Ratios of Mortality for HF Subjects in Chronic HF Study II

| | Galectin-3 Hazard Ratio (95% CI, p value) | |
|---|---|---|
| | less than or equal to 17.6 ng/mL | greater than 17.6 ng/mL |
| Number of subjects | 114 | 118 |
| Model 1 (univariate) | 1.0 | 1.57 (1.05-2.35, p = 0.029) |
| Model 2 (adjusted for age and gender) | 1.0 | 1.52 (1.01-2.27, p = 0.044) |
| Number of deaths at 40 months | 29/114 (25.4%) | 45/118 (38.1%) |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

```
Sequence total quantity: 12
SEQ ID NO: 1            moltype = AA  length = 113
FEATURE                 Location/Qualifiers
source                  1..113
                        mol_type = protein
                        organism = Homo sapiens
SEQUENCE: 1
MADNFSLHDA LSGSGNPNPQ GWPGAWGNQP AGAGGYPGAS YPGAYPGQAP PGAYPGQAPP  60
GAYPGAPGAY PGAPAPGVYP GPPSGPGAYP SSGQPSATGA YPATGPYGAP AGP         113

SEQ ID NO: 2            moltype = AA  length = 10
FEATURE                 Location/Qualifiers
VARIANT                 7..10
                        note = MISC_FEATURE - Xaa at positions 7-10 may be any
                         naturally occurring amino acid and up to three of them may
                         be absent
source                  1..10
                        mol_type = protein
                        organism = Homo sapiens
SEQUENCE: 2
PGAYPGXXXX                                                         10

SEQ ID NO: 3            moltype = AA  length = 12
FEATURE                 Location/Qualifiers
source                  1..12
                        mol_type = protein
                        organism = Homo sapiens
SEQUENCE: 3
MADNFSLHDA LS                                                      12

SEQ ID NO: 4            moltype = AA  length = 14
```

-continued

```
FEATURE               Location/Qualifiers
source                1..14
                      mol_type = protein
                      organism = Homo sapiens
SEQUENCE: 4
MADNFSLHDA LSGS                                                 14

SEQ ID NO: 5          moltype = AA  length = 11
FEATURE               Location/Qualifiers
source                1..11
                      mol_type = protein
                      organism = Homo sapiens
SEQUENCE: 5
GNPNPQGWPG A                                                    11

SEQ ID NO: 6          moltype = AA  length = 10
FEATURE               Location/Qualifiers
source                1..10
                      mol_type = protein
                      organism = Homo sapiens
SEQUENCE: 6
WGNQPAGAGG                                                      10

SEQ ID NO: 7          moltype = AA  length = 18
FEATURE               Location/Qualifiers
source                1..18
                      mol_type = protein
                      organism = Homo sapiens
SEQUENCE: 7
YPGQAPPGAY PGQAPPGA                                             18

SEQ ID NO: 8          moltype = AA  length = 16
FEATURE               Location/Qualifiers
source                1..16
                      mol_type = protein
                      organism = Homo sapiens
SEQUENCE: 8
YPGAPGAYPG APAPGV                                               16

SEQ ID NO: 9          moltype = AA  length = 19
FEATURE               Location/Qualifiers
source                1..19
                      mol_type = protein
                      organism = Homo sapiens
SEQUENCE: 9
YPGAPAPGVY PGPPSGPGA                                            19

SEQ ID NO: 10         moltype = AA  length = 12
FEATURE               Location/Qualifiers
source                1..12
                      mol_type = protein
                      organism = Homo sapiens
SEQUENCE: 10
YPSSGQPSAT GA                                                   12

SEQ ID NO: 11         moltype = AA  length = 31
FEATURE               Location/Qualifiers
source                1..31
                      mol_type = protein
                      organism = Homo sapiens
SEQUENCE: 11
YPGAPAPGVY PGPPSGPGAY PSSGQPSATG A                              31

SEQ ID NO: 12         moltype = AA  length = 4
FEATURE               Location/Qualifiers
source                1..4
                      mol_type = protein
                      organism = synthetic construct
SEQUENCE: 12
CGPC                                                            4
```

What is claimed is:

1. A method for quantitatively determining a level of galectin-3 in a sample from a subject, the method comprising the steps of:

obtaining from the subject at least one sample comprising whole blood, serum, or plasma;

contacting the at least one sample with a first binding moiety comprising an M3/38 monoclonal antibody immobilized on a solid surface, wherein the M3/38 monoclonal antibody binds to a first epitope located within an N-terminal region of human galectin-3 and captures the human galectin-3 in the at least one sample to form a first complex;

contacting the first complex with a second binding moiety comprising a 87B5 monoclonal antibody and a detectable label, wherein the 87B5 monoclonal antibody binds a second epitope located within the N-terminal region of human galectin-3 that does not overlap with the first epitope, thereby forming a sandwich complex comprising the detectable label;

detecting the detectable label of the second complex to generate a signal proportional to the concentration of human galectin-3 in the sample, determining the concentration of human galectin-3 in the biological sample by comparing the signal to a calibration curve generated using known concentrations of human galectin-3;

wherein the method selectively detects human galectin-3 relative to other galectins present in the biological sample; and determining that the subject has an increased risk of development or progression of heart failure when the level of the human galectin-3 exceeds a threshold of at least 15 ng/ml.

2. The method of claim 1, wherein the threshold is 15-20 ng/ml.

3. The method of claim 1, wherein the threshold is 20-25 ng/ml.

4. The method of claim 1, wherein the threshold is 25-30 ng/ml.

5. The method of claim 1, wherein the threshold is 30-35 ng/ml.

6. The method of claim 1, further comprising repeating the method over time to obtain a trend.

* * * * *